US007309602B2

(12) United States Patent
David

(10) Patent No.: US 7,309,602 B2
(45) Date of Patent: *Dec. 18, 2007

(54) COMPOSITIONS AND METHODS FOR PRODUCING FERMENTATION PRODUCTS AND RESIDUALS

(75) Inventor: Peter R. David, Palo Alto, CA (US)

(73) Assignee: AmbroZea, Inc., Palo Alto, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/383,748

(22) Filed: May 16, 2006

(65) Prior Publication Data

US 2007/0243592 A1  Oct. 18, 2007

Related U.S. Application Data

(60) Provisional application No. 60/797,431, filed on May 3, 2006, provisional application No. 60/744,833, filed on Apr. 13, 2006.

(51) Int. Cl.
C12N 1/19 (2006.01)
A23B 7/10 (2006.01)
A23B 7/154 (2006.01)
C12P 7/06 (2006.01)

(52) U.S. Cl. ............... 435/254.2; 435/161; 435/256; 426/53; 426/56

(58) Field of Classification Search ............... None
See application file for complete search history.

(56) References Cited

U.S. PATENT DOCUMENTS

| | | | |
|---|---|---|---|
| 4,567,145 A | 1/1986 | Faber et al. | |
| 4,828,846 A | 5/1989 | Rasco et al. | |
| 5,145,695 A | 9/1992 | Smith et al. | |
| 5,151,354 A * | 9/1992 | Strasser et al. | ........ 426/11 |
| 5,219,596 A | 6/1993 | Smith et al. | |
| 5,480,805 A | 1/1996 | Wolf et al. | |
| 5,530,188 A | 6/1996 | Ausich et al. | |
| 5,656,319 A | 8/1997 | Barclay | |
| 5,656,472 A | 8/1997 | Ausich et al. | |
| 5,766,925 A | 6/1998 | Sugimoto et al. | |
| 6,410,755 B1 | 6/2002 | Millis et al. | |
| 6,538,182 B1 | 3/2003 | Thompson et al. | |
| 6,774,284 B1 | 8/2004 | Thompson et al. | |
| 6,849,782 B2 | 2/2005 | Thompson et al. | |
| 6,855,529 B2 | 2/2005 | Thompson et al. | |
| 6,867,237 B1 | 3/2005 | Taylor et al. | |
| 6,878,860 B1 | 4/2005 | Thompson et al. | |
| 7,001,610 B2 | 2/2006 | Stewart | |
| 2002/0155192 A1 | 10/2002 | Walker et al. | |
| 2003/0049241 A1 | 3/2003 | Jocobson et al. | |
| 2003/0104587 A1 | 6/2003 | Verser et al. | |
| 2003/0157675 A1 | 8/2003 | Cordero Otero e al. | |
| 2004/0248280 A1 * | 12/2004 | Bolla et al. | ........ 435/254.2 |
| 2006/0008546 A1 | 1/2006 | de Souza et al. | |
| 2006/0039955 A1 | 2/2006 | Messman et al. | |
| 2006/0057251 A1 | 3/2006 | Dawley et al. | |
| 2006/0286645 A1 | 12/2006 | Li et al. | |
| 2007/0037267 A1 * | 2/2007 | Lewis et al. | ........ 435/161 |

FOREIGN PATENT DOCUMENTS

| | | |
|---|---|---|
| EP | 0450430 A2 | 10/1991 |
| EP | 0450430 A3 | 10/1991 |
| WO | WO 2002/03812 A2 | 1/2002 |
| WO | WO 2002/03812 A3 | 1/2002 |
| WO | WO 2005/118795 A2 | 12/2005 |
| WO | WO 2005/118795 A3 | 12/2005 |

OTHER PUBLICATIONS

Parekh et al., Pilot-scale production of butanol by *Clostridium beijerinckii* BA101 using low-cost fermentation medium based on corn steep water. Appl Microbiol Biotechnol. 1999 51:152-157.*
Romanos et al., Yeast vol. 8, Issue 6, pp. 423-488, 1992.*
Zeikus J.G. Chemical and fuel production by anaerobic bacteria. Annu Rev Microbiol. 1980;34:423-64.*
Birkelo, et al. The energy content of wet corn distillers grains for lactating dairy cows. J Dairy Sci. 2004; 87(6):1815-9.
Casey, et al. High Gravity Brewing: Effects of Nutrition on Yeast Compostition, Fermentative Ability, and Alcohol Production. Appl Environ Microbiol. 1984: 48(3):639-646.

(Continued)

*Primary Examiner*—Joseph Woitach
*Assistant Examiner*—Maria Leavit
(74) *Attorney, Agent, or Firm*—Wilson Sonsini Goodrich & Rosati

(57) ABSTRACT

The present invention provides compositions and methods designed to increase value output of a fermentation reaction. In particular, the present invention provides a business method of increasing value output of a fermentation plant. The present invention also provides a modified fermentation residual of higher commercial value. Also provided in the present invention are complete animal feeds, nutritional supplements comprising the subject ferment residuals. Further provided by the present invention is a method of performing fermentation, a modified fermentative microorganism and a genetic vehicle for modifying such microorganism.

24 Claims, 2 Drawing Sheets

OTHER PUBLICATIONS

Coon, C The present and future utilization of biotechnology in the feed industry: a poultry nutritionist's perspective. University Of Arkansas. Available at http://www.asa-europe.org/pdf/present.pdf. Accessed Oct. 16, 2006.

Feed-Use Amino Acids Business. Ajinomoto Co., Inc. Oct. 2006. 6 pages.

Gasent-Ramirez, et al. Lysine-overproducing mutants of *Saccharomyces cerevisiae* baker's yeast isolated in continous culture. Appl Environ Microbiol. 1997; 63(12):4800-6.

Hao, C. T. J. Yeast dilution. Bachelor of engineering thesis presented at The University of Queensland on May 19, 2004. 39 pages.

Ingledew, W. M. Yeast—could you base business on this bug? In T.P. Lyons and K.A. Jacques, editors. Under the miccroscope—Focal Points for the New Millennium-Biotechnology in the Feed Industry. Proceedings of Alltech's 15th Annual Symposium. Nottingham University Press, Nottingham, UK. 1999. pp. 27-47.

Ingledew, W. M. Improvements in alcohol technology through advancements in fermentation technology. Getreidetechnologie (Getreidetechnologie).2005; 59(5):308-311.

Larkins, B. A. Boosting lysine improves nutritional value of corn. US Department of Agriculture. Cooperative State Research, Education, and Extension Service. 2001 No. 4. 2 pages.

Lyons, et al. (Ed) Biotechnology in the Feed Industry. Proceedings of Alltech's 10th Annual Symposium. Nottingham University Press. Loughtorough, Leicestershire, UK. 1994. (Table of Contents only).

Mason, S. Rumen-protected amino acids. Available at http://www.westerndairyscience.com/html/CALRT%20articles/html/Aa1.html. Accessed Oct. 11, 2006.

Meyers, et al. trans-Recessive mutation in the first structural gene of histidine operon that results in a constitutive expression of the operon. J. Bacteriology 1975, 124 (3) 1227-1235.

Moller, K. Glucose metabolism in the petite-negative yeast *Saccharomyces kluyveri*. Ph. D. thesis presented Technical University of Denmark. 2001. 132 pages.

Nagai, et al. Transcriptional regulation of the heat shock regulatory gene rpoH in *Escherichia coli*: involvement of a novel catabolite-sensitive promoter. J. Bacteriol. 1990; 172(5):2710-2715.

National Renewable Energy Laboratory. The DOE bioethanol pilot plant—A tool for commercialization. DOE/GO-102000-1114. Sep. 2000. 4 pages.

Nutrient Requirements of Beef Cattle. 7th Revised Edition. National Academy Press. Washington, D. C. 1996 (Table of Contents only). 2 pages.

Nutritional Requirements of Dairy Cattle. 7th Revised Edition. National Acedemy Press. Washington, D.C. 2001. (Table of Contents only). 2 pages.

Nutritional Requirements of Swine. 10th Revised Edition. National Academy Press. Washington, D.C. 1998. (Table of Contents only). 9 pages.

O'Connor-Cox, et al. Wort nitrogenous sources—Their use by brewing yeasts: A review. J. Am. Soc. Brew. Chem. 1989; 120-108.

Potera, C. Progress with biofuels will depend on, drive microbology research—As interest in biofuels surges, finding cost-effective ways fo converting biomass to fuels and feedstocks poses challenges to microbiologists. Microbe. 2006; 1(7):317-322.

Program and Abstracts. 27th Symposium on Biotechnology for fuels and chemicals hosted by the National Renewable Energy Laboratory in Denver Marriott City Center Hotel, Denver, Colorado May 1-4, 2005.

Sambrook, et al. Molecular cloning: A laboratory manual. Cold Spring Harbor Labs Press. Planview, NY. 1989. Table of Contents only. 30 pages.

Shimazu, et al. A Family of Basic Amino Acid Transporters of the Vacuolar Membrane from *Saccharomyces cerevisiae*. J. Biol. Chem. 2005; 280(6)4851-4857.

Shurson, et al. Corn By-Product Diversity and Feeding Value to Non-Ruminants. Minnesota Nutrition Conference Proceedings. 2005; 19 pages.

Shurson, et al. Nutritional and value added benefits of maize DDGS and other dry-mill co-products to swine. University of Minnesota. Eastern Nutrition Conf., Ottawa, Ontario, Canada. May 10-11, 2004. 20 pages.

Soto, et al. Estimation of ethanol yield in corn mash fermentations using mass of ash as a marker. Journal of the Institute of Brewing, 2005; 111(2):137-143.

Thomas, et al. Effects of particulate materials and osmoprotectants on very-high-gravity ethanolic fermentation by *Saccharomyces cerevisiae*. Appl Environ Microbiol. 1994; 60(5):1519-24.

Thomas, et al. Fuel alcohol production: effects of free amino nitrogen on ferementation on very-high-gravity wheat mashes. Appl Environ Microbiol. 1990;56(7):2046-50.

Thomas, et al. Production of fuel alcohol from hull-less barley by very high gravity technology. Cereal Chemistry. 1995; 72(4):360-364.

Thomsen, et al. Biotechnology in ethanol production. In Risø Energy Report 2. 2003; 40-44.

Widyaratne, G. P. Characterization and improvement of the nutritional value of ethanol by-products for swine. Master of science degree thesis presented at University of Saskatchenwan. Dec. 2005. 140 pages.

Cereghino, et al. Heterologous protein expression in the methylotropic yeast *Pichia pastoris*. FEMS Microbiology Reviews. 2000; 24:45-66.

Dansen, et al. Regulation of sterol carrier protein gene expression by the Forkhead transcription factor FOXO3a. J. Lipid Research. 2004; 45:81-88.

He, et al. Overexpression of a sterol C-24(28) reductase increases ergosterol production in *Saccharomyces cerevisiae*. Biotechnology Letters. 2003; 25(10):773-8.

Kim, et al. A role in vacuolar arginine transport for yeast Btn1p and for human CLN3, the protein defective in Batten disease. PNAS. 2003; 100:15458-15462.

Rippert, et al. Engineering Plant Shikimate Pathway for Production of Tocotrienol and Improving Herbicide Resistance. Plant Physiol. 2004; 134:92-100.

Stepanova, et al. Lysine Overproduction Mutations in the Yeast *Saccharomyces cerevisiae* Are Introduced into Industrial Yeast Strains. Russian J. Genetics. 2001; 37:460-463.

Sychrova, et al. Kinetic properties of yeast lysine permeases coded by genes on multi-copy vectors. FEMS Microbiol Lett. 1993; 113(1):57-61.

Szczebara, et al. Total biosynthesis of hydrocortisone from a simple carbon source in yeast. Nat Biotechnol. 2003;21(2):143-9.

Misawa, et al. Production of β-carotene in Zymomonas mobilis and Agrobacterium tumefaciens by intoduction of the biosynthesis genes from Erwinia uredovora. Applied and Environmental Microbiology. 1991; 57(6): 1847-9.

Foreign Search Report of Jul. 2, 2007 Reguarding Application No. GB0706778.8.

* cited by examiner

COMPOSITIONS AND METHODS FOR PRODUCING FERMENTATION PRODUCTS AND RESIDUALS

CROSS REFERENCE

This application claims the benefit of U.S. Provisional Application No. 60/744,833 filed Apr. 13, 2006, U.S. Provisional Application No. 60/797,431 filed May 3, 2006, all of which are incorporated herein by reference in their entirety.

BACKGROUND OF THE INVENTION

The ethanol fuel industry is growing at a rapid pace. Numerous federal and state incentives, such as clean burning fuel programs, have fostered the exponential growth of more than five times over the past two decades. In 2004, high oil prices, a bumper corn crop, and limited processing capacity created new market opportunities and resulted in record production of more than 3.4 billion gallons of fuel ethanol. Today, ethanol represents the third largest market for U.S. corn. At this pace, fuel ethanol production is positioning itself as an integral part of rural economic development and environmental improvement.

Ethanol can be made through fermentation and distillation of starch found in crops such as corn, sorghum, potatoes, sugar cane, as well as in cornstalks. Ethanol is usually produced in either dry grind or wet mill facilities. The primary co-products generated from the wet mills or "corn refineries" include high fructose corn syrup, corn oil, gluten feed, and gluten meal. Co-products from the dry grind process include distillers grains and carbon dioxide. While both types of facilities have similar operating costs, the dry grind facilities are usually smaller and require a lower initial investment, making their capital costs two to four times less per gallon. The dry mill types of ethanol production process the starch portion of corn, which is about 60% of the kernel. All the remaining nutrients—protein, fat, minerals, and vitamins—are concentrated into distillers grain which is a valuable feed for livestock. A bushel of corn weighing nearly 56 pounds may produce approximately 2.8 gallons of ethanol and 18 pounds of distillers grain.

Distillers grain can provide a high quality feedstuff ration for dairy cattle, beef cattle, swine, poultry, pets, and aquaculture. The feed is an economical partial replacement for corn, soybean meal, and dicalcium phosphate in livestock and poultry feeds. Distillers grain continues to be an excellent, economical feed ingredient for use in ruminant diets. DDGS (distillers dried grains with solubles) production has been expected to double from 3.5 million metric tons in 2002 to over 7 million metric tons by 2006. The sale of distillers grain is an important part of the total profitability and growth of the ethanol industry. If dried distillers grain sales lag behind the increasing production of ethanol, the current ethanol industry could be significantly affected. An effective marketing of distillers grain as animal feed will undoubtedly contribute to the efficiency and overall profitability of an ethanol facility.

Current ethanol production schemes by fermentation are far from being optimized. While efforts have been directed to improve ethanol production, little research has been focused on enhancing the value output of the fermentation residuals including the distillers grain that contributes to a significant portion of the animal feed market.

Thus, there remains a considerable need for compositions and methods that are designed to increase the value output of a fermentation facility. An ideal fermentation scheme would maintain the high ethanol production, and at the same time yield fermentation residuals of higher commercial value. The present invention satisfies this need and provides related advantages as well.

SUMMARY OF THE INVENTION

The present invention provides compositions and methods designed to increase value output of a fermentation reaction. In one embodiment, the present invention provides a business method of increasing value output of a fermentation plant. The method comprises the steps of (a) performing a fermentation reaction with the use of a modified microorganism; and (b) marketing or selling one or more of the products of the fermentation reaction comprising said modified microorganism. In a related embodiment, the method of increasing value output of a fermentation plant comprises performing a fermentation reaction using carbon-containing material in the presence of a modified microorganism to yield fermentation residual that has a higher commercial value than if the fermentation reaction were performed in the absence of the modified microorganism. In one aspect, the fermentation reaction can be performed under either aerobic or anaerobic conditions. The fermentation reaction typically produces products such as alcohol, including but not limited to methanol, ethanol, propanol, and butanol, as well as gaseous co-products such as carbon dioxide. In addition, the fermentation reaction also yields residuals that are of higher commercial value than conventional fermentation residuals. In another aspect, the fermentation reaction may utilize any carbon-containing starting material, e.g., carbohydrates that are present in a wide variety of substances, including but not limited to cellulose, wood chips, vegetables, biomass, excreta, animal wastes, oat, wheat, corn, barley, milo, millet, rice, rye, sorghum, potato, sugar beets, taro, cassava, fruits, fruit juices, and sugar cane. The modified microorganism employed in the subject methods can be eukaryotic (e.g., yeast) or prokaryotic (e.g., bacteria or archaebacteria). In a preferred embodiment, the fermentation reaction yields fermentation residuals that have an enhanced nutritional content. In one aspect of this embodiment, the fermentation residuals are enriched in one or more types of cofactors, hormones, proteins, preservatives, stabilization agents, nutraceuticals, vitamins, essential amino acids, and/or lipids. In some aspects, the reaction is performed with the subject microorganisms to increase the value output of the entire fermentation reaction by enhancing the process to yield more valuable products and/or fermentation residuals. In some other aspects, the reaction is performed with the subject microorganisms to increase the value output without substantially decreasing the amount of fermentation products produced by the fermentation reaction, and/or without substantially decreasing the total values of fermentation products produced by the fermentation reaction.

The present invention also provides a fermentation residual comprising a genetically modified microorganism, wherein the fermentation residual has a commercial value (e.g. due to increase in nutritional content) higher than that of a fermentation residual that is deficient in said modified microorganism. In one aspect, the subject fermentation residual has a shelf life that is longer than that of a fermentation residual that is deficient in said modified microorganism. In another aspect, the residual is enriched in at least one essential amino acid, a significant faction of which (e.g. the majority of which) is encapsulated in a cell (e.g., a prokaryotic or eukaryotic cell used in the fermentation reaction). Where desired, at least about 25%, or preferably 50%, preferably at least about 60%, or even more preferably at least about 80% of the essential amino acids measured by dry weight are encapsulated in a cell or spore. In addition, the essential amino acids may be embodied in a homologous polypeptide with enhanced concentration, or a heterologous polypeptide produced by a microorganism used in the fermentation reaction. The heterologous polypeptide can be secretory or preferably non-secretory (e.g., in a vacuole when the polypeptide is in an inclusion body within the fermentation microorganism). The heterologous polypeptide enriched in essential amino acid sequences can adopt a variety of structural conformations such as a beta-sheet conformation, an alpha-helix conformation, a random-coil conformation, and/or a coiled-coil conformation, or an aggregate, or a combination thereof.

Depending on the intended use, the essential amino acid may exclude histidine and include any one of the exemplary essential amino acids. Non-limiting exemplary essential amino acids include lysine, methionine, threonine, methionine, phenylalanine, and arginine. The quantity of essential amino acid present in the residuals may vary from at least about 0.25%, 1%, at least about 2%, at least about 3% to about 95% by dry weight.

The subject fermentation residuals can be supplemented with a desirable flavor tailored for one or more types of animals. The residuals can also be packaged with instructions for use as animal feed or food supplement for humans.

The present invention further provides a modified microorganism whose nutritional content increases by a greater extent than that of an unmodified corresponding microorganism when used in a fermentation reaction. In some instances, if the nutritional content increases due to an increase in at least one essential amino acid, then the at least one essential amino acid is not histidine. In a related but separate embodiment, the present invention also provides a modified microorganism whose nutritional content is enhanced as compared to an unmodified corresponding microorganism when used in a fermentation reaction and when the fermentation reaction has achieved at least about 50% completion. In another embodiment, the present invention provides a modified microorganism producing an alcohol product in a fermentation reaction that utilizes a carbon-containing starting material, wherein said microorganism also produces a nutrient subsequent to the initiation of the alcohol production In another embodiment, the present invention provides a modified microorganism that comprises an exogenous sequence encoding a polypeptide, wherein the polypeptide comprises at least one essential amino acid, and wherein expression of the exogenous sequence is induced when the fermentation reaction has achieved at least about 50% completion. In yet another embodiment, the present invention provides a modified microorganism comprising an exogenous sequence encoding a polypeptide that comprises at least one essential amino acid, and wherein expression of the exogenous sequence is under the control of a glucose suppressor operon.

The progression of fermentation can be monitored by a variety of ways. For example, at least 50% completion of a fermentation reaction can be evidenced by the consumption of at least 50% of the total glucose in the desired fermentation, when compared to similar fermentations, or when 50% of the total glucose has been added, or when the total amount of carbon dioxide emitted, and dissolved is 50% of the total amount emitted in similar fermentations. More specifically, at least 50% completion of a fermentation reaction can be evidenced by a decrease in glucose content to less than about 50% of the initial content of glucose present in a fermentation reaction mixture (i.e., the glucose level present prior to the beginning of the fermentation reaction), or less than a desired threshold level (e.g., about 100 grams per liter fermentation reaction). Alternatively, the degree of completion can be determined by the amount of time during which the fermentation has taken place, typically, at least about half the time taken by a similar fermentation. The duration of fermentation time may range from about 1 hour to several days, depending on the relevant amounts of microorganisms and fermentation starting material provided. One skilled in the art can readily ascertain the normal duration of a fermentation reaction without undue experimentation when given the amount of microorganisms and starting materials.

The modified microorganism can be a eukaryote (e.g., yeast) or a prokaryote (e.g., bacteria or archaebateria). It can be modified to overproduce a nutritional component including but not limited to amino acid, vitamin, and/or lipid. This is typically achieved by genetically modifying the metabolic pathway of the microorganism for producing such nutritional component, and/or directly introducing an exogenous sequence that encodes the nutritional component (e.g., a particular type of amino acid contained in a polypeptide). Where desired, genetic modification can be carried out with the use of genetic vehicles that carry one or more of the metabolic pathway gene sequences, or the sequences that code for the exogenous polypeptides carrying the nutritional component such as essential amino acids. A wide variety of genetic vehicles are applicable for such use. They include an array of expression vectors including both viral and non-viral vectors. In a preferred embodiment, expression of the exogenous sequence is under the control of a regulatory sequence selected from the group consisting of a regulatory sequence of a heat shock gene, regulatory sequence of a toxicity gene, regulatory sequence of a spore formation gene, and glucose suppressor operon. When regulated under these sequences, the increase in production of the nutritional component by the microorganisms can be induced at a time when the fermentation has substantially been completed, preferably at least about 50% completed, more preferably at least about 70% completed, more preferably about 90% completed. Such regulation allows production of fermentation products of enhanced nutritional value and maximizing the profit from the fermentation reaction.

The present invention further provides a method of fermentation using carbon-containing material. The method typically comprises the steps of (a) mixing a carbon-containing material with a modified microorganism of the present invention, and (b) subjecting the mixture of (a) to conditions suitable for production of a fermentation product. Where desired, the method can further comprise the step of harvesting one or more fermentation products. Exemplary fermentation products include alcohol such as methanol, ethanol, propanol, butanol and the like, as well as gaseous products such as carbon dioxide. The fermentation method can be performed under aerobic or anaerobic conditions. A wide variety of carbon-containing raw materials can be used in the fermentation reaction. Exemplary materials include but are not limited to cellulose, oat, wheat, corn, milo, millet, barley, rice, rye, sorghum, potato, sugar beets, taro, cassaya, fruits, fruit juices, and sugar cane.

Further embodied in the present invention is an expression vector suitable for modifying the subject microorganism. The expression vector typically comprises an exogenous sequence encoding a polypeptide that comprises at least one essential amino acid, wherein expression of the exogenous sequence is induced when the fermentation reaction has achieved at least about 50% completion. Where desired, the expression vector comprises one or more of the following regulatory sequences so as to control the expression of the exogenous polypeptide. Exemplary regulatory sequences include glucose suppressor operon, a regulatory sequence of a heat shock gene, regulatory sequence of a toxicity gene, or regulatory sequence of a spore formation gene.

The present invention also embodies variations and all combination of the composition and methods described herein.

INCORPORATION BY REFERENCE

All publications and patent applications mentioned in this specification are herein incorporated by reference to the same extent as if each individual publication or patent application was specifically and individually indicated to be incorporated by reference.

BRIEF DESCRIPTION OF THE DRAWINGS

The illustrations included within this specification describe many of the advantages and features of the invention. It shall be understood that similar reference numerals and characters noted within the illustrations herein may designate the same or like features of the invention. The illustrations and features depicted herein are not necessarily drawn to scale.

DETAILED DESCRIPTION OF THE INVENTION

Figure 1:
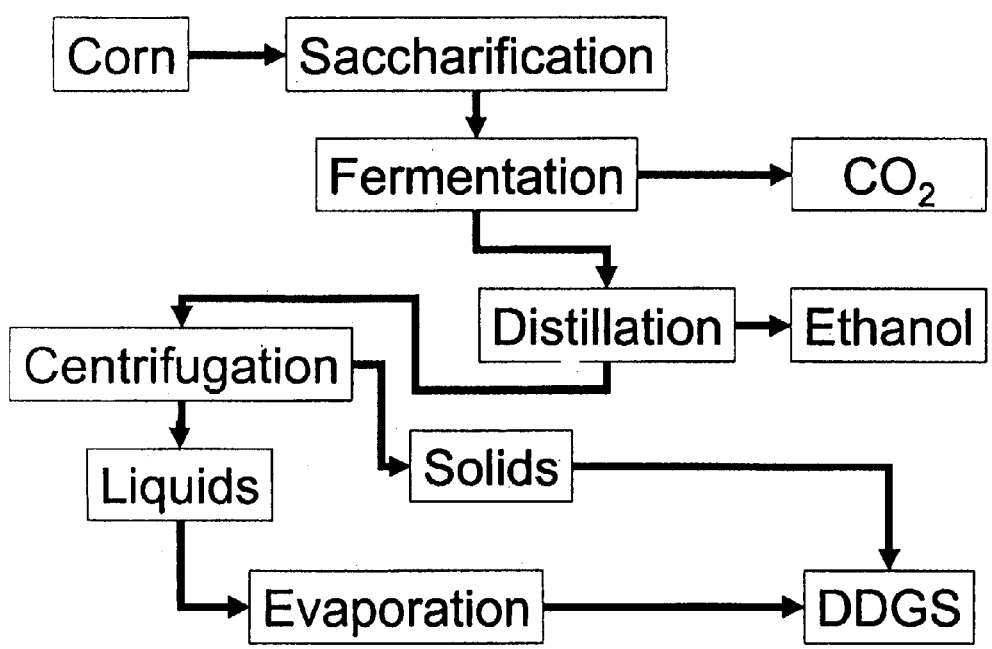
FIG. 1 is a flow chart describing an exemplary ethanol production process that results in formation of ethanol, carbon dioxide, and fermentation residuals such as distillers dried grain with solubles or solids (DDGS).
Figure 2:
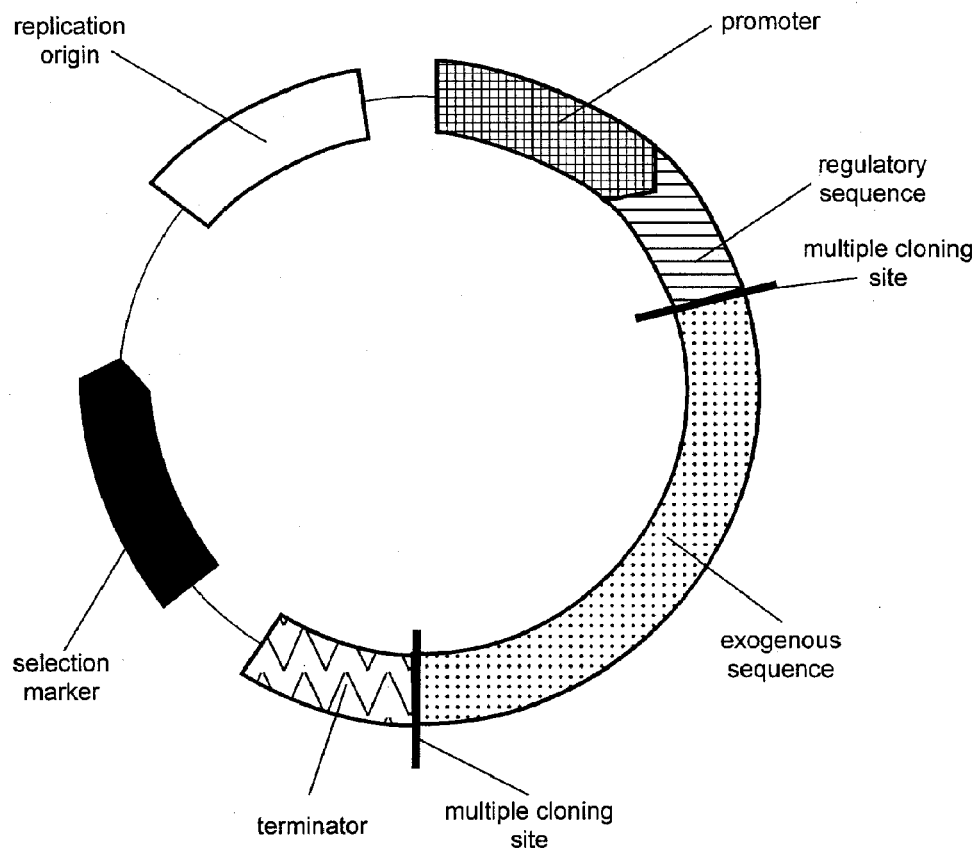
FIG. 2 is a schematic representation of an exemplary genetic vehicle useful for modifying a microorganism used in the subject fermentation reaction.

While preferred embodiments of the invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention.

The term "animal" means any organism belonging to the kingdom Animalia and includes, without limitation, poultry, cattle, swine, goat, sheep, cat, dog, mouse, aquaculture, horse, etc.

The term "fermentation residuals" as used herein means any residual substances directly resulting from a fermentation reaction. In some instances, a fermentation residual contains modified microorganisms such that it has a nutritional content enhanced as compared to a fermentation residual that is deficient in such modified microorganism. The fermentation residuals may contain suitable constituent(s) from a fermentation broth. For example, the fermentation residuals may include dissolved and/or suspended constituents from a fermentation broth. The suspended constituents may include undissolved soluble constituents (e.g., where the solution is supersaturated with one or more components) and/or insoluble materials present in the fermentation broth. The fermentation residuals may include substantially all of the dry solids present at the end of a fermentation (e.g., by spray drying a fermentation broth and the biomass produced by the fermentation) or may include a portion thereof. The fermentation residuals may include crude fermentation product from fermentation where a modified-microorganism may be fractionated and/or partially purified to increase the nutrient content of the material.

The term "fatty acid" as used herein means an aliphatic or aromatic monocarboxylic acid.

The term "lipids" as used herein means fats or oils including without limitation the glyceride esters of fatty acids along with associated phosphatides, sterols, alcohols, hydrocarbons, ketones, and related compounds.

The term "nutrient" as used herein means any substances with nutritional value. It can be part of an animal feed or food supplement for humans. Exemplary nutrients include but are not limited to fats, fatty acids, lipids such as phospholipid, vitamins, essential amino acids, peptides, proteins, carbohydrates, sterols, enzymes, and trace minerals such as, iron, copper, zinc, manganese, cobalt, iodine, selenium, molybdenum, nickel, fluorine, vanadium, tin, and silicon. The nutrient may be secreted by a modified microorganism in a fermentation broth or contained within the microorganism. (e.g. in inclusion bodies in the microorganism.) The nutrient may also be added to the feed containing the fermentation residuals.

"Heterologous polypeptide" or "heterologous protein" means derived from (i.e., obtained from) a genotypically distinct entity from the rest of the entity to which it is being compared, or that it is genetically indistinct but produced at an abnormally high or low concentration as compared to a native unmodified environment or microorganism.

The term "unsaturated fatty acid" as used herein means a fatty acid with 1 to 3 double bonds and a "highly unsaturated fatty acid" means a fatty acid with 4 or more double bonds.

Fermentation Process

Fermentation as used herein can be anaerobic (deficient in oxygen) as well as aerobic (oxygenated). Under aerobic conditions, microorganisms such as yeast cells can break down sugars to end products such as $CO_2$ and $H_2O$. Under anaerobic conditions, yeast cells utilize an alternative pathway to produce $CO_2$ and ethanol. The fermentation reaction of the present invention is preferably anaerobic, i.e., partially or completely deficient in oxygen. Fermentation can also be used to refer to the bulk growth of microorganisms on a growth medium where no distinction is made between aerobic and anaerobic metabolism.

The present invention also encompasses methane fermentation. Methane fermentation can convert all types of polymeric materials to methane and carbon dioxide under anaerobic conditions. This may be achieved as a result of the consecutive biochemical breakdown of polymers to methane and carbon dioxide in an environment in which a variety of microorganisms including fermentative microbes (acidogens), hydrogen-producing, acetate-forming microbes (acetogens), and methane-producing microbes (methanogens), grow harmoniously and produce the reduced end-products.

Methane fermentation is the consequence of a series of metabolic interactions among various groups of microorganisms. The microorganisms secrete enzymes that fragment polymeric materials and hydrolize the polymers and fragments to monomers such as glucose and amino acids, which are subsequently converted to higher volatile fatty acids, $H_2$, and acetic acid. In the second stage, hydrogen-producing acetogenic bacteria convert the higher volatile fatty acids e.g., propionic and butyric acids, produced, to $H_2$, $CO_2$, and acetic acid. Finally, the third group, methanogenic bacteria convert $H_2$, $CO_2$, and acetate, to $CH_4$, and $CO_2$. Polymeric materials such as lipids, proteins, and carbohydrates can be primarily hydrolyzed by extracellular, hydrolases, excreted by microorganisms. Hydrolytic enzymes, (lipases, proteases, cellulases, amylases, etc.) may hydrolyze their respective polymers into smaller molecules, primarily monomeric units, which can then be consumed by microorganisms.

Enzymes such as, lipases may convert lipids to long-chain fatty acids. Clostridia and the micrococci are the examples of extracellular lipase producers. Proteins can be generally hydrolyzed to amino acids by proteases, secreted by *Bacteroides, Butyrivibrio, Clostridium, Fusobacterium, Selenomonas*, and *Streptococcus*. The amino acids produced can then be degraded to fatty acids such as acetate, propionate, and butyrate, and to ammonia as found in *Clostridium, Peptococcus, Selenomonas, Campylobacter*, and *Bacteroides*.

Polysaccharides such as cellulose, starch, and pectin can be hydrolyzed by cellulases, amylases, and pectinases. Most anaerobic bacteria undergo hexose metabolism via the Emden-Meyerhof-Pamas pathway (EMP) which produces pyruvate as an intermediate along with NADH. The pyruvate and NADH thus generated, can then be transformed into fermentation endo-products such as lactate, propionate, acetate, and ethanol by other enzymatic activities which may vary with microorganism species.

Thus, in hydrolysis and acidogenesis, sugars, amino acids, and fatty acids produced by microorganism by degradation of biopolymers are metabolised to fermentation endo-products such as lactate, propionate, acetate, carbon dioxide, and ethanol by other enzymatic activities which vary with microorganism species. Methanogens such as, *Methanosarcina* spp. and *Methanothrix* spp ., are also methane producers in anaerobic digestion. Although acetate and $H_2/CO_2$ are the main substrates available in the natural environrent, formate, methanol, methylamines, and CO can also be converted to $CH_4$.

FIG. 1 is a flowchart diagram of an ethanol manufacturing process that results in the production of fermentation residuals that include but are not limited to distillers dried grain with solubles or solids (DDGS) in accordance with the invention. Many feed products can result from the ethanol manufacturing process that often utilizes corn as the starting material for example as illustrated, but it should be understood that other carbohydrate or starch sources such as other grain products can also be incorporated with the invention.

There are a variety of carbon sources that can be used in the fermentation process of the present invention. The raw material for most commercial alcohol production includes for example, corn, wheat, milo, oat, barley, rice, rye, sorghum, potato, whey, sugar beets, taro, cassaya, fruits, fruit juices, and sugar cane. The carbon sources used in the fermentation process of the present invention can be natural, chemically modified, or genetically modified. The examples of the carbon source that may be fermented by modified-microorganisms of the present invention, include, but are not limited to, corn, canola, alfalfa, rice, rye, sorghum, sunflower, wheat, soybean, tobacco, potato, peanut, cotton, sweet potato, cassaya, coffee, coconut, citrus trees, cocoa, tea, fruits such as, banana, fig, pineapple, guava, mango, oats, barley, vegetables, ornamentals, and conifers. Preferable carbon source are crop plants for example, cereals and pulses, maize, wheat, milo, oats, amaranth, rice, sorghum, millet, cassaya, barley, pea, tapioca, taro, potatoes, and other root, tuber, or seed crops. A biomass in the form of wastes from agriculture such as corn stover, rice straw, manure, etc., and biomass crops such as switch grass or poplar trees, and even municipal wastes such as newspaper can all be converted into alcohol. The carbon source can include any appropriate carbon source such as wood, waste paper, manure, cheese whey, molasses, sugar beets or sugar cane. This carbon source can also include unhydrolyzed corn syrup or starch which is an inexpensive carbon source.

A preferred carbon-containing starting material for fermentation is corn. Corn is about two-thirds starch, which is converted during a fermentation and distilling process into ethanol and carbon dioxide. The remaining nutrients or fermentation residuals can result in condensed distillers solubles or distillers grains such as DDGS, which can be used in feed products. In general, the process involves an initial preparation step of dry milling or grinding of the corn. The processed corn is then subject to hydrolysis and enzymes added to break down the principal starch component in a saccharification step. The following step of fermentation is allowed to proceed upon addition of a modified microorganism (e.g. yeast) provided in accordance with an embodiment of the invention to produce gaseous products such as carbon dioxide. The fermentation is conducted for the production of ethanol which can be distilled from the fermentation broth. The remainder of the fermentation medium can be then dried to produce fermentation residuals including DDGS. This step usually includes a solid/liquid separation process by centrifugation wherein a solid phase component can be collected. Other methods including filtration and spray dry techniques can be employed to effect such separation. The liquid phase components can be subjected further afterwards to an evaporation step that can concentrate soluble coproducts, such as sugars, glycerol and amino acids, before being recombined with the solid phase component to be dried as fermentation residuals. It shall be understood that the subject compositions and can be applied to new or already existing ethanol plants based on dry milling to provide an integrated ethanol production process that also produces fermentation residuals with increased value.

A preferable fermentation residuals produced according to the present invention has a higher commercial value than the conventional fermentation residuals. For example, the fermentation residuals can include enhanced dried solids such as DDGS with improved amino acid and micronutrient content. A "golden colored" DDGS product can be thus provided which generally indicates higher amino acid digestibility compared to darker colored DDGS. For example, a light-colored DDGS can be produced with an increased lysine concentration in accordance with a preferable embodiment herein compared to a relatively darker colored products with generally less nutritional value. The color of the products tends to be an important factor or indicator in the assessing the quality and nutrient digestibility of the fermentation residuals or DDGS. Color is used as an indicator of exposure to excess heat during drying causing caramelization and Millard reactions of the free amino groups and sugars, reducing the quality of some amino acids.

The basic steps in a dry mill or grind ethanol manufacturing process as shown in FIG. 1 may be described as follows: milling or grinding of corn or other grain product, saccharification, fermentation, and distillation. For example, selected whole corn kernels can be milled or ground with typically either hammer mills or roller mills. The particle size can influence cooking hydration and subsequent enzymatic conversion. The milled or ground corn can be then mixed with water to make a mash that is cooked and cooled. It may be useful to include enzymes during the initial steps of this conversion to decrease the viscosity of the gelatinized starch. The mixture can be then transferred to saccharification reactors, maintained at selected temperatures such as 104 degrees F., where the starch is converted by addition of saccharifying enzymes to fermentable sugars such as glucose or maltose. The converted mash can be cooled to desired temperatures such as 84 degrees F., and fed to fermentation reactors where fermentable sugars are converted to carbon dioxide by the use of selected strains of enhanced yeasts provided in accordance with the invention that results in more nutritional fermentation residuals compared to more traditional ingredients such as *Saccharomyces* yeasts. The resulting beer can be flashed to separate out carbon dioxide and the resulting liquid can be fed to a recovery system consisting of distillation columns and a stripping column. The ethanol stream can be directed to a molecular sieve where remaining water is removed using adsorption technology. Purified ethanol, denatured with a small amount of gasoline, can produce fuel grade ethanol. Another product can be produced by further purifying the initial distillate ethanol to remove impurities, resulting in about 99.95% ethanol for non-fuel uses.

The whole stillage can be withdrawn from the bottom of the distillation unit and centrifuged to produce distillers wet grains (DWG) and thin stillage (liquids). The DWG can leave the centrifuge at 55-65% moisture, and can either be sold wet as a cattle feed or dried as enhanced fermentation residuals provided in accordance with the invention. These residuals include an enhanced end product that may be referred to herein as distillers dried grains (DDG). Using an evaporator, the thin stillage (liquid) can be concentrated to form distillers solubles, which can be added back to and combined with a distillers grains process stream and dried. This combined product in accordance with a preferable embodiment of the invention can be marketed as an enhanced fermentation residual or distillers dried grains with solubles (DDGS) having increased amino acid and micronutrient content. It shall be understood that various concepts of the invention can be applied to other ethanol manufacturing and fermentation processes known in the field other than those illustrated herein.

Animal Feed

Another aspect of the present invention is directed towards complete animal feeds with an enhanced concentration of nutrients which includes modified microorganisms characterized by an enhanced concentration of nutrients such as, but not limited to, fats, fatty acids, lipids such as phospholipid, vitamins, essential amino acids, peptides, proteins, carbohydrates, sterols, enzymes, and trace minerals such as, iron, copper, zinc, manganese, cobalt, iodine, selenium, molybdenum, nickel, fluorine, vanadium, tin and silicon.

Fermentation Residuals

In a fermentation process of the present invention, a carbon source may be hydrolyzed to its component sugars by modified-microorganisms to produce alcohol and other gaseous products. Gaseous product includes carbon dioxide and alcohol includes ethanol. The fermentation residuals obtained after the fermentation reaction are typically of higher commercial value. In one aspect, the fermentation residuals contain modified microorganisms that have enhanced nutrient content than those residuals deficient in the modified microorganisms. The modified microorganisms may be present in a fermentation system, the fermentation broth and/or fermentation biomass. The fermentation broth and/or biomass may be dried (e.g., spray-dried), to produce the fermentation residuals with an enhanced content of the nutritional contents.

For example, the spent, dried solids recovered following the fermentation process are enhanced in accordance with the invention to provide improved DDG or DDGS (commonly referred to as distillers dried grain with solubles). These fermentation residuals are generally non-toxic, biodegradable, readily available, inexpensive, and rich in nutrients. The choice of microorganism and the fermentation conditions are important to produce a low toxicity or non-toxic fermentation residual for use as a feed or nutritional supplement. While glucose is the major sugar produced from the hydrolysis of the starch from grains, it is not the only sugar produced in carbohydrates generally. Unlike the DDG produced from the traditional dry mill ethanol production process, which contains a large amount of non-starch carbohydrates (e.g., as much as 35% percent of cellulose and arabinoxylans-measured as neutral detergent fiber, by dry weight), the subject nutrient enriched fermentation residuals produced by enzymatic hydrolysis of the non-starch carbohydrates are more palatable and digestible to the non-ruminant.

The composition of nutrient enriched fermentation residuals of the present invention may be different from that of DDG and other distillers' co-products produced from the traditional dry mill ethanol production process, which are obtained through the fermentation of the starch present in whole, ground corn without the subject modified microorganisms. The nutrient enriched fermentation residual of this invention may have a nutrient content of from at least about 1% to about 95% by weight. The nutrient content is preferably in the range of at least about 10%-20%, 20%-30%, 30%-40%, 40%-50%, 50%-60%, 60%-70%, and 70%-80% by weight. The available nutrient content may depend upon the animal to which it is fed and the context of the remainder of the diet, and stage in the animal life cycle. For instance, beef cattle require less histidine than lactating cows. Selection of suitable nutrient content for feeding animals is well known to those skilled in the art.

The fermentation residuals may be prepared as a spray-dried biomass product. Optionally, the biomass may be separated by known methods, such as centrifugation, filtration, separation, decanting, a combination of separation and decanting, ultrafiltration or microfiltration. The biomass fermentation residuals may be further treated to facilitate rumen bypass. In one embodiment, the biomass product may be separated from the fermentation medium, spray-dried, and optionally treated to modulate rumen bypass, and added to feed as a nutritional source. In addition to producing nutritionally enriched fermentation residuals in a fermentation system containing modified microorganisms, the nutritionally enriched fermentation residuals may also be produced in transgenic plant systems. Methods for producing transgenic plant systems are known in the art. Alternatively, where the modified microorganism host excretes the nutritional contents, the nutritionally-enriched broth may be separated from the biomass produced by the fermentation and the clarified broth may be used as an animal feed ingredient, e.g., either in liquid form or in spray dried form.

The fermentation residuals obtained after the fermentation reaction using modified microorganisms can be used as an animal feed or as food supplement for humans. The fermentation residual includes at least one ingredient that has an enhanced nutritional content that is derived from a non-animal source (e.g., a bacteria, yeast, and/or plant). In particular, the fermentation residuals are rich in at least one or more of fats, fatty acids, lipids such as phospholipid, vitamins, essential amino acids, peptides, proteins, carbohydrates, sterols, enzymes, and trace minerals such as, iron, copper, zinc, manganese, cobalt, iodine, selenium, molybdenum, nickel, fluorine, vanadium, tin and silicon. Preferably, the peptides contain at leas one essential amino acid. Preferably, the essential amino acids are encapsulated inside a subject modified microorganism used in a fermentation reaction. More preferably, the essential amino acids are contained in heterologous polypeptides expressed by the microorganism. Where desired, the heterologous polypeptides are expressed and stored in the inclusion bodies in a suitable fermentative microorganism (e.g., yeast).

Animal Feed Compositions

In one aspect, the subject modified fermentation residuals have a high nutritional content. As a result, a higher percentage of the fermentation residuals can be used in a complete animal feed. In some embodiments, the feed composition comprises at least about 15% of fermentation residual by weight. In a complete feed, or diet, this material will be fed with other materials. Depending upon the nutritional content of the other materials, and/or the nutritional requirements of the animal to which the feed is provided, the modified fermentation residuals may range from 15% of the feed to 100% of the feed. In some embodiments, the subject fermentation residuals may provide lower percentage blending due to high nutrient content. In other embodiments, the subject fermentation residuals may provide very high fraction feeding, e.g. over 75%. In suitable embodiments, the feed composition comprises at least about 20%, at least about 25%, at least about 30%, at least about 35%, at least about 40%, at least about 45%, at least about 50%, at least about 60%, at least about 70%, or at least about 75% of the subject fermentation residuals. Commonly, the feed composition comprises at least about 20% of fermentation residual by weight. More commonly, the feed composition comprises at least about 15-25%, 25-20%, 20-25%, 30%-40%, 40%-50%, 50%-60%, or 60%-70% by weight of fermentation residual. Where desired, the subject fermentation residuals may be used as a sole source of feed, particularly for domestic poultry (e.g. chicken, ducks and geese) and pigs.

The complete animal feed may have enhanced amino acid content with regard to one or more essential amino acids for a variety of purposes, e.g., for milk production, for weight increase and overall improvement of the animals' health. The complete animal feed may have an enhanced amino acid content because of the presence of free amino acids and/or the presence of proteins or peptides including an essential amino acid, in the fermentation residuals. Essential amino acids may include histidine, lysine, methionine, phenylalanine, threonine, isoleucine, and/or tryptophan, which may be present in the complete animal feed as a free amino acid or as part of a protein or peptide that is rich in the selected amino acid. At least one essential amino acid-rich peptide or protein may have at least 1% essential amino acid residues per total amino acid residues in the peptide or protein, at least 5% essential amino acid residues per total amino acid residues in the peptide or protein, or at least 10% essential amino acid residues per total amino acid residues in the protein. By feeding a diet balanced in nutrients to animals, maximum use is made of the nutritional content, requiring less feed to achieve comparable rates of growth, milk production, or a reduction in the nutrients present in the excreta reducing bioburden of the wastes.

A complete animal feed with an enhanced content of an essential amino acid, may have an essential amino acid content (including free essential amino acid and essential amino acid present in a protein or peptide) of at least 2.0 wt. % relative to the weight of the crude protein and total amino acid content, and more suitably at least 5.0 wt. % relative to the weight of the crude protein and total amino acid content. The complete animal feed composition includes other nutrients derived from modified-microorganisms including but not limited to, fats, fatty acids, lipids such as phospholipid, vitamins, carbohydrates, sterols, enzymes, and trace minerals.

The complete animal feed composition may include complete feed form composition, concentrate form composition, blender form composition, and base form composition. If the composition is in the form of a complete feed, the percent nutrient level, where the nutrients are obtained from the modified microorganism in a fermentation residual, which may be about 10 to about 25 percent, more suitably about 14 to about 24 percent; whereas, if the composition is in the form of a concentrate, the nutrient level may be about 30 to about 50 percent, more suitably about 32 to about 48 percent. If the composition is in the form of a blender, the nutrient level in the composition may be about 20 to about 30 percent, more suitably about 24 to about 26 percent; and if the composition is in the form of a base mix, the nutrient level in the composition may be about 55 to about 65 percent. Unless otherwise stated herein, percentages are stated on a weight percent basis. If the DDGS is high in a single nutrient, e.g. Lys, it will be used as a supplement at a low rate; if it is balanced in amino acids and Vitamins, e.g. vitamin A and E, it will be a more complete feed and will be fed at a higher rate and supplemented with a low protein, low nutrient feed stock, like corn stover.

The feed composition may include a peptide or a crude protein fraction present in a fermentation residual having an essential amino acid content of at least about 2%. In suitable embodiments, a peptide or crude protein fraction may have an essential amino acid content of at least about 3%, at least about 5%, at least about 10%, at least about 15%, at least about 20%, at least about 30%, at least about 40%, and in suitable embodiments, at least about 50%]. In some embodiments, the peptide may be 100% essential amino acids. Commonly, the feed composition may include a peptide or crude protein fraction present in a fermentation residual having an essential amino acid content of up to about 10%. More commonly, the feed composition may include a peptide or a crude protein fraction present in a fermentation residual having an essential amino acid content of about 2-10%, 3.0-8.0%, or 4.0-6.0%.

The feed composition may include a peptide or a crude protein fraction present in a fermentation residual having a lysine content of at least about 2%. In suitable embodiments, the peptide or crude protein fraction may have a lysine content of at least about 3%, at least about 5%, at least about 10%, at least about 15%, at least about 20%, at least about 30%, at least about 40%, and in suitable embodiments, at least about 50%. Typically, the feed composition may include the peptide or crude protein fraction having a lysine content of up to about 10%. Where desired, the feed composition may include the peptide or a crude protein fraction having a lysine content of about 2-10%, 3.0-8.0%, or 4.0-6.0%.

The feed composition may include nutrients in the fermentation residual from about 1 g/Kg dry solids to 900 g/Kg dry solids. In some embodiments, the nutrients in a feed composition may be present to at least about 2 g/Kg dry solids, 5 g/Kg dry solids, 10 g/Kg dry solids, 50 g/Kg dry solids, 100 g/Kg dry solids, 200 g/Kg dry solids, and about 300 g/Kg dry solids. In suitable embodiments, the nutrients may be present to at least about 400 g/Kg dry solids, at least about 500 g/Kg dry solids, at least about 600 g/Kg dry solids, at least about 700 g/Kg dry solids, at least about 800 g/Kg dry solids and/or at least about 900 g/Kg dry solids.

The feed composition may include an essential amino acid or a peptide containing at least one essential amino acid present in a fermentation residual having a content of about 1 g/Kg dry solids to 900 g/Kg dry solids. In some embodiments, the essential amino acid or a peptide containing at least one essential amino acid in a feed composition may be present to at least about 2 g/Kg dry solids, 5 g/Kg dry solids, 10 g/Kg dry solids, 50 g/Kg dry solids, 100 g/Kg dry solids, 200 g/Kg dry solids, and about 300 g/Kg dry solids. In suitable embodiments, the essential amino acid or a peptide containing at least one essential amino acid may be present to at least about 400 g/Kg dry solids, at least about 500 g/Kg dry solids, at least about 600 g/Kg dry solids, at least about 700 g/Kg dry solids, at least about 800 g/Kg dry solids and/or at least about 900 g/Kg dry solids.

The feed composition may include a rumen-protected amino acid source of non-animal origin which may include rumen-protected lysine or other essential amino acids and/or a rumen-protected amino acid-rich protein or peptide, more preferably an essential amino acid rich protein or peptide. The free essential amino acid or essential amino acid rich protein or peptide may be rumen-protected by reacting with at least one reducing carbohydrate (e.g., a reducing sugar) or with at least one fatty acid. Suitable reducing carbohydrates may include xylose, lactose, and/or glucose. Suitable fatty acids may include at least partially hydrogenated vegetable oils, such as soybean oil. The rumen-protected amino acid source may be capable of delivering at least about 40% of rumen-protected amino acid post-ruminally. More commonly, the rumen-protected amino acid source may be capable of delivering at least about 50%, 60%, 70%, 80%, or 90% of rumen-protected amino acid post-ruminally.

The complete animal feed composition may contain a nutrient enriched fermentation residual in the form of a biomass formed during fermentation and at least one additional nutrient component. In another example, the feed composition contains a nutrient enriched fermentation residual that is dissolved and suspended from a fermentation broth formed during fermentation and at least one additional nutrient component. In a further embodiment, the feed composition has a crude protein fraction that includes at least one essential amino acid-rich protein. The feed composition may be formulated to deliver an improved balance of essential amino acids post-ruminally.

The complete feed form composition may contain one or more ingredients such as wheat middlings ("wheat mids"), corn, soybean meal, corn gluten meal, distillers grains or distillers grains with solubles, salt, macro-minerals, trace minerals and vitamins. Other potential ingredients may commonly include, but not be limited to sunflower meal, malt sprouts and soybean hulls. The blender form composition may contain wheat middlings, corn gluten meal, distillers grains or distillers grains with solubles, salt, macro-minerals, trace minerals and vitamins. Alternative ingredients would commonly include, but not be limited to, corn, soybean meal, sunflower meal, cottonseed meal, malt sprouts and soybean hulls. The base form composition may contain wheat middlings, corn gluten meal, and distillers grains or distillers grains with solubles. Alternative ingredients would commonly include, but are not limited to, soybean meal, sunflower meal, malt sprouts, macro-minerals, trace minerals and vitamins (Messman et al. U.S. Pub. No. 2006/0039955, which is incorporated herein in its entirety).

Highly unsaturated fatty acids (HUFAs) in modified microorganisms, when exposed to oxidizing conditions can be converted to less desirable unsaturated fatty acids or to saturated fatty acids. However, saturation of omega-3 HUFAs can be reduced or prevented by the introduction of synthetic antioxidants or naturally-occurring antioxidants, such as beta-carotene, vitamin E and vitamin C, into the feed. Synthetic antioxidants, such as BHT, BHA, TBHQ or ethoxyquin, or natural antioxidants such as tocopherols, can be incorporated into the food or feed products by adding them to the products, or they may be incorporated by in situ production in a suitably modified organism. The amount of antioxidants incorporated in this manner depends, for example, on subsequent use requirements, such as product formulation, packaging methods, and desired shelf life.

Fermentation residual or complete feed containing the fermentation residual of the present invention, can also be utilized as a nutritional supplement for human consumption if the process begins with human grade input materials, and human food quality standards are observed through out the process. Fermentation residual or the complete feed as disclosed in the invention is high in nutritional content. Nutrients such as, protein and fiber are associated with healthy diets. Recipes can be developed to utilize fermentation residual or the complete feed of the invention in foods such as cereal, crackers, pies, cookies, cakes, pizza crust, summer sausage, meat balls, shakes and in any forms of edible food. Another choice can be to develop the fermentation residual or the complete feed of the invention into snacks or a snack bar, similar to a granola bar that could be easily eaten, convenient to distribute. A snack bar may include protein, fiber, germ, vitamins, minerals, from the grain, as well as nutraceuticals such as glucosame, HUFAs, or co-factors, such as Vitamin Q-10. The nutritional fermentation residual of the invention can also be incorporated into domestic food programs such as school lunches and meals on wheels.

The animal feed and food supplement for human comprising the subject fermentation residuals can be further supplemented with desirable flavors. The choice of a particular flavor will depend on the animal to which the feed is provided. The flavors and aromas, both natural and artificial, may be used in making feeds more acceptable and palatable. These supplementations may blend well with all ingredients and may be available as a liquid or dry product form. Suitable flavors and aromas to be supplemented in the animal feeds include but not limited to fenugreek, banana, cherry, rosemary, cumin, carrot, peppermint oregano, vanilla, anise, plus rum, maple, caramel, citrus oils, ethyl butyrate, anethol, apple, cinnamon, any natural or artificial combinations thereof. In general, flavors including fenugreek, banana, and cherry are highly desirable for horses, vanilla maple and anise for cows, and rum, berry and coconut for pigs. The favors and aromas may be interchanged between different animals. Similarly, a variety of fruit flavors, artificial or natural can be added to food supplements comprising the subject fermentation residuals for human consumption.

Shelf-Life

The shelf-life of the fermentation residual or the complete feed of the present invention can typically be longer than the shelf life of a fermentation residual that is deficient in modified microorganism. The shelf-life may depend on factors such as, the moisture content of the product, how much air can flow through the feed mass, the environmental conditions and the use of preservatives. A preservative can be added to the complete feed to increase the shelf life to weeks and months. Other methods to increase shelf life include management similar to silage management such as mixing with other feeds and packing, covering with plastic or bagging. Cool conditions, preservatives and excluding air from the feed mass all extend shelf life of wet co-products. The complete feed can be stored in bunkers or silo bags. Drying the wet fermentation residual or complete feed may also increase the product's shelf life and improve consistency and quality.

The complete feed of the present invention can be stored for long periods of time. The shelf life can be extended by ensiling, adding preservatives such as organic acids, or blending with other feeds such as soy hulls. Commodity bins or bulk storage sheds can be used for storing the complete feeds.

Modified Microorganisms

Suitable microorganisms that can be used in the fermentation reaction of the present invention include prokaryotic and eukaryotic cell cultures. Preferred microorganisms produce a low toxicity or non-toxic fermentation residuals for use as a feed or nutritional supplement. Preferred biological systems include fungal, bacterial, and microalgal systems. More preferred biological systems are fungal cell cultures, more preferably a yeast cell culture, and most preferably a *Saccharomyces cerevisiae* cell culture. Fungi can be manipulated by both classical microbiological and genetic engineering techniques. The preferred prokaryote is *E. coli*. Preferred microalga for use in the present invention includes *Chlorella* and Protetheca. Some of the examples of yeast that can be modified for the fermentation process disclosed herein include by way of example only, *Saccharomyces cerevisiae*, *Saccharomyces carlsbergensis*, *Kluyveromyces lactis*, *Saccharomyces lactis*, *K. marxianus*, or *K. fragilis* yeasts, and *Brettanomyces* sp. etc. Some of the examples of bacteria that can be modified for the fermentation process disclosed herein include by way of example only, *Zymomonas* sp., *E. coli*, *Corynebacterium. Brevibacterium, Bacillus* ssp. etc. The fermentation can be a homoacetic fermentation using an acetogen such as a microorganism of the genus *Clostridium*, e.g., microorganisms of the species *Clostridium thermoaceticum* or *Clostridium formicoaceticum*. The fermentation can be lactic acid fermentation using a microorganism of the genus *Lactobacillus*. Alternatively, the carbohydrate source can be converted into lactic acid, lactate, acetic acid, acetate, or mixtures thereof in an initial fermentation using a bifido bacterium.

The microorganism is modified in such a way that the modified microorganism has enhanced nutritional content. The modified microorganism may be enriched in nutrients like, by way of example only, fats, fatty acids, lipids such as phospholipid, vitamins, essential amino acids, peptides, proteins, carbohydrates, sterols, enzymes, and trace minerals such as, iron, copper, zinc, manganese, cobalt, iodine, selenium, molybdenum, nickel, fluorine, vanadium, tin and silicon. The fatty acids include saturated and unsaturated fatty acids where unsaturated fatty acids include omega-3 highly unsaturated fatty acid. The examples of omega-3 highly unsaturated fatty acid include, but are not limited to, eicosapentaenoic acid, docosapentaenoic acid, alpha linolenic acid, docosahexaenoic acid, and conjugates thereof.

Alternatively, algae or fungi, for example, Thraustochytrium, Schizochytrium etc. can ferment ground, hydrolyzed, or unhydrolyzed grain to produce omega-3 HUFAs. It can be used for any type of grain, including without limitation, corn, milo, sorghum, rice, wheat, oats, rye and millet. This process further includes alternative use of unhydrolyzed corn syrup or agricultural/fermentation products such as stillage, a waste product in corn to alcohol fermentations, as an inexpensive source. Grains and waste products can be hydrolyzed by any method known in the art, such as acid hydrolysis or enzymatic hydrolysis (Barclay, William R. U.S. Pat. No. 5,656,319, incorporated herein by reference in its entirety one or more types and/or strains of microorganisms for parallel or sequential fermentation. Without limitation, an example is fermentation with yeast secreting alpha amylase to hydrolyze starch, followed by a yeast to ferment the glucose into ethanol.

Other examples of the microorganism include, but are not limited to, fungus *Blakeslea trispora*, *Dunaliella salina*, *Phaffia rhodozyma*, *Haematococcus pluvialis*, genus *Flavobacterium*, *Agrobacterium aurantiacum*, *Erwinia herbicola* or *Erwinia uredovora*, genus *Paracoccus*, *Agrobacterium*, and *Alcaligenes* etc.

Where desired, strains of bacteria or yeast may be selected for the production of palatable flavors. For example, the subject microorganisms may be modified in such a way that one or more of flavor enhancers are produced by the microorganisms. Flavor enhancers may be derived from yeast RNA. Yeasts like *Candida* can be grown with as much as 15% RNA. *Saccharomyces* yeasts can be used to make flavor active compounds. Nucleosides such as, inosine-5'-monophosphate and quanosine-5'-monophosphate which in combination with monosodium glutamate can be used for flavor improvement.

In some embodiments, the microorganisms that have been modified to enhance alcohol or alkane production in a fermentation reaction can be further modified according to the subject methods to yield the subject microorganisms having an enhanced nutritional content.

In some embodiments of the present invention, the subject microorganisms may be modified in such a way that one or more of pigments or colorants are produced by the microorganism. Some yeasts for example, Phaffia rhodozyma produce a pink pigment called astaxanthin. Astaxanthin is the natural color found in lobsters, shrimp, salmon and in flamingos. The whole yeast or complete animal feed of the present invention can be fed to fish or crustaceans reared in captivity, where they rarely gain the natural color, thereby providing the characteristic flesh color to the salmon or seafood to improve marketability. At the same time, the other nutrients provided by the yeast are also of benefit to the fish.

Modification of Microorganism

In some embodiments, the modified microorganism useful for a fermentation reaction comprises a chemically modified or a genetically modified microorganism. Preferably the cells used in the cell culture are genetically modified by genetic engineering techniques (i.e., recombinant technology), classical microbiological techniques, or a combination of such techniques and can also include naturally occurring genetic variants. Some of such techniques are generally disclosed, for example, in Sambrook et al., 1989, Molecular Cloning: A Laboratory Manual, Cold Spring Harbor Labs Press. The reference Sambrook et al., ibid., is incorporated by reference herein in its entirety.

A genetically modified microorganism can include a microorganism in which nucleic acid molecules have been inserted, deleted or modified (i.e., mutated; e.g., by insertion, deletion, substitution, and/or inversion of nucleotides), in such a manner that such modifications provide the desired effect of increased yields of nutrients within the microorganism or in the culture supernatant. As used herein, genetic modifications that result in a decrease in gene expression, in the function of the gene, or in the function of the gene product (i.e., the nutrient such as, protein encoded by the gene) can be referred to as inactivation (complete or partial), deletion, interruption, blockage or down-regulation of a gene. For example, a genetic modification in a gene which results in a decrease in the function of the protein encoded by such gene, can be the result of a complete deletion of the gene (i.e., the gene does not exist, and therefore the protein does not exist), a mutation in the gene which results in incomplete or no translation of the protein (e.g., the protein is not expressed), or a mutation in the gene which decreases or abolishes the natural function of the protein (e.g., a protein is expressed which has decreased or no enzymatic activity). Genetic modifications which result in an increase in gene expression or function can be referred to as amplification, overproduction, overexpression, activation, enhancement, addition, or up-regulation of a gene. Addition of cloned genes to increase gene expression can include maintaining the cloned gene(s) on replicating plasmids or integrating the cloned gene(s) into the genome of the production organism. Furthermore, increasing the expression of desired cloned genes can include operatively linking the cloned gene(s) to native or heterologous transcriptional control elements.

A microorganism may be modified by methods known in the art and they are with in the scope of the invention. By way of example only, the method includes manipulating at least one of the structural genes in the nutrients' biosynthetic pathway, optionally manipulating the regulatory controls of the synthetic pathway, and optionally manipulating the nutrients' transport processes out of and into the microorganism. For example, the microorganism may have mutations in a particular gene for amino acid biosynthesis. The method preferably includes manipulating at least one of the structural genes to regulate synthesis of a peptide containing at least one essential amino acid.

The subject microorganisms can be modified to overproduce a nutrient such as an essential amino acid, vitamin, hormone, protein, and/or lipid. Where desired, the production of one or more nutrients is under the control of a regulatory sequence that controls directly or indirectly the production in a time-dependent fashion during a fermentation reaction. Preferably, the regulatory sequences directly or indirectly control the production such that the desired nutrient is produced when the fermentation reaction has reached a desired percentage of completion, preferably at least about 50% of completion, more preferably at least about 60% completion, and more preferably at least about 70% to about 90% completion, and even more preferably at least about 95% completion. When controlled in this manner, the yield of fermentation products such as alcohol and gaseous products is unlikely to be affected.

In some embodiments, the invention includes a modified microorganism useful for a fermentation reaction, comprising an exogenous sequence encoding a polypeptide which comprises at least one essential amino acid residue, wherein expression of the exogenous sequence is under the control of a regulatory sequence. Preferably, the regulatory sequences directly or indirectly suppress expression of the exogenous sequence until the fermentation reaction has reached a desired percentage of completion, preferably at least about 50% of completion, more preferably at least about 60% completion, and more preferably at least about 70% to about 90% completion, and even more preferably at least about 95% completion. A variety of suitable regulatory sequences can be employed in the present invention. Non-limiting examples include glucose suppressor operon that normally suppresses expression of the exogenous gene when operably linked together until fermentation has reached for instance at least 50% of completion, as well as a wide range of regulatory sequences from heat shock genes (e.g., rpoH gene as described in Nagai et al. *J. Bacteriol.* 1990 May; 172(5): 2710-2715), toxicity genes, and spore formation genes. In particular, the initiation of glucose suppressor operon may cause induction of an expression of the exogenous sequence encoding a desired polypeptide. The glucose suppressor operon may be initiated when the fermentation reaction has achieved at least about 50% completion. The fermentation reaction can be monitored by monitoring the glucose content of the fermentation mixture or by monitoring the amount of the gaseous product formed during the fermentation reaction.

A polynucleotide is said to encode a polypeptide if, in its native state or when manipulated by methods known to those skilled in the art, it can be transcribed and/or translated to produce the polypeptide or a fragment thereof. The anti-sense strand of such a polynucleotide is also said to encode the sequence.

In some embodiments, a modified microorganism is induced with a genetic vehicle such as, an expression vector comprising an exogenous sequence encoding a polypeptide comprising at least one essential amino acid residue. Polynucleotide constructs prepared for introduction into a prokaryotic or eukaryotic host may typically, but not always, comprise a replication system (i.e. vector) recognized by the host, including the intended polynucleotide fragment encoding the desired polypeptide, and may preferably, but not necessarily, also include transcription and translational initiation regulatory sequences operably linked to the polypeptide-encoding segment. Expression systems (expression vectors) may include, for example, an origin of replication or autonomously replicating sequence (ARS) and expression control sequences, a promoter, an enhancer and necessary processing information sites, such as ribosome-binding sites, RNA splice sites, polyadenylation sites, transcriptional terminator sequences, and mRNA stabilizing sequences. Signal peptides may also be included where appropriate, preferably from secreted polypeptides of the same or related species, which allow the protein to cross and/or lodge in cell membranes or be secreted from the cell.

A vast number of genetic vehicles suitable for the present invention are available in the art. They include both viral and non-viral expression vectors. Non-limiting exemplary viral expression vectors are vectors derived from RNA viruses such as retroviruses, and DNA viruses such as adenoviruses and adeno-associated viruses. Non-viral expression vectors include but are not limited to plasmids, cosmids, and DNA/liposome complexes. Where desired, the genetic vehicles can be engineered to carry regulatory sequences that direct organelle specific expression of the exogenous genes carried therein. For example, leader or signal sequence can be added to direct the exogenous sequence to inclusion bodies of a suitable microorganism. The genetic vehicles can be inserted into a host microorganism by any of a number of appropriate means, including electroporation, transfection employing calcium chloride, rubidium chloride, calcium phosphate, DEAE-dextran, or other substances, microprojectile bombardment, lipofection, and infection.

The expression vector could be employed for any amino acid or peptide and can be used in the case of *E. coli*, yeast, or other microorganisms to increase the amino acid or peptide production. Preferably, the peptide consists of at least one essential amino acid.

Variants or sequences having substantial identity or homology with the polynucleotides encoding enzymes may be utilized in the practice of the invention. Such sequences can be referred to as variants or modified sequences. That is, a polynucleotide sequence may be modified yet still retain the ability to encode a polypeptide exhibiting the desired activity. Such variants or modified sequences are thus equivalents. Generally, the variant or modified sequence may comprise at least about 40%-60%, preferably about 60%-80%, more preferably about 80%-90%, and even more preferably about 90%-95% sequence identity with the native sequence.

The genetic control of synthesis of the galactose pathway enzymes in *Saccharomyces cerevisiae* conforms in certain respects to the operon model for the β-galactoside system of *E. coli*. For example, in *E. coli*, free histidine represses the operon through feed back inhibition of the first enzyme in the pathway, adenosine 5'-triphosphate phosphoribosyltransferase, HisG. Mutation of the hisG gene in *S. typhimurium* may result in a 3-4 times increase in the intracellular concentration of the histidine operon enzymes. (See Meyers et al., J. Bacteriology 1975, 124 (3) 1227-1235).

Yeast may be a particularly suitable host for expressing a particular amino acid-rich peptide or protein and/or free amino acids. In lysine-accumulating yeast, the majority of the lysine may be contained in vacuoles that are stable when incubated with rumen fluid, but immediately released when exposed to pepsin, one of the protein-digesting enzymes of the abomasum. Thus, this organism may be a useful host for expressing proteins and/or amino acids and providing a protected feed supplement that may increase the amount of proteins and/or amino acids available for intestinal absorption. The amino acid may include, by way of example only, lysine, histidine, methionine, phenylalanine, and threonine. The amino acid-rich products may be produced by methods known in the art. For example, a lysine-rich fermentation broth may be used as a source of lysine. The lysine-rich fermentation broth may be produced by single-cell organisms (e.g., microorganisms such as bacteria or yeast) that are selected or engineered to overproduce lysine. Suitable microorganisms may include microorganisms belonging to the genus *Saccharomyces cerevisiae*, *Eschrichia*, *Bacillus*, *Microbacteriur*, *Arthrobacter*, *Serratia*, and *Corynebacterium*. As such Gram-negative bacteria, such as *E. coli* may be suitable for producing a histidine broth.

It may be desirable to use microbial hosts that do not contain lipopolysaccharides ("LPS") that have endotoxic effects, for example a Gram-positive bacteria, such as *Corynebacteria* and *Brevibacterium*. Gram-negative bacteria, such as *E. coli*, often include LPS that have an endotoxic effect. Selection of a bacteria that does not include endotoxic LPS may be particularly important when a biomass is to be prepared and used as an amino acid source, because the majority of LPS remain associated with bacteria and are not released substantially into the fermentation broth unless the bacteria are lysed. As such, endotoxic LPS would be expected to be localized within the biomass after fermentation.

A particular amino acid-rich protein or peptide may be over-expressed in a microbial host (such as a species of Eschrichia, *Corynebacterium*, *Brevibacterium*, *Bacillus*, Yeast), plants and the like. In some embodiments, the amino acid-rich protein is composed of essential and non-essential amino acids. In some preferred embodiments, the amino acid-rich protein is composed of essential amino acid/s only. A particular amino acid-rich protein may be selected from those amino acid-rich proteins described in the literature, for example, a histadine-rich protein II from *Plasmodium falciparum* and one or more of the proteins from class of proteins called "histatins," which demonstrate anti-bacterial and anti-fungal activities (Mervyn et al. U.S. Pub No. 2006/0008546, incorporated herein by reference in its entirety). A particular amino acid-rich protein may also comprise specific fragments of known amino acid-rich proteins that have an increased content of that particular amino acid compared to the full-length protein. For example, a histidine-rich protein II from *Plasmodium falciparum* has a histidine composition of about 32%. The fragment of this protein from amino acid 61 to 130 has a histidine composition of about 44%. The fragment of this protein from amino acid 58 to 80 has a histidine composition of about 55%. Another exemplary class of proteins comprises lysine-rich proteins. Exemplary lysine-rich proteins include natural, recombinant and/or synthetic sequences. Any one of the proteins or fragment thereof listed in Table 1 can be expressed by the subject microorganisms. An amino acid-rich protein does not need to retain its native function to be suitable for the compositions or methods described herein.

TABLE 1

Exemplary Lysine-Rich Proteins

| Protein Name | UniProtKB/Swiss-Pro Primary Accession Number |
| --- | --- |
| ribosomal protein L44 | P17843 |
| 40S ribosomal protein S27a | P29504 |
| 40S ribosomal protein S27a | P47905 |
| 40S ribosomal protein S27a (bovine) | P62992 |
| 40S ribosomal protein S27a (guinea pig) | P62978 |
| 40S ribosomal protein S27a (human) | P62979 |
| 40S ribosomal protein S27a *Plutella xylostella* | P68202 |
| 40S ribosomal protein S27a (*Kluyveromyces lactis* (Yeast)) | P69061 |
| 40S ribosomal protein S27a (*Gallus gallus* (Chicken)) | P79781 |
| 40S ribosomal protein S27a (*Mus musculus* (Mouse)) | P62983 |
| 40S ribosomal protein S27a (*Rattus norvegicus* (Rat)) | P62982 |
| 40S ribosomal protein S27a (*Spodoptera frugiperda* (Fall armyworm)) | P68203 |
| 60S ribosomal protein L44 (*Arabidopsis thaliana* (Mouse-ear cress)) | O23290 |
| 40S ribosomal protein S27a-1 (*Arabidopsis thaliana* (Mouse-ear cress)) | P59271 |
| 40S ribosomal protein S27a (*Ictalurus punctatus* (Channel catfish)) | P68200 |
| 40S ribosomal protein S27a (*Asparagus officinalis* (Garden asparagus)) | P31753 |
| 40S ribosomal protein S27a-3 (*Arabidopsis thaliana* (Mouse-ear cress)) | P59233 |
| 40S ribosomal protein S27a (*Drosophila melanogaster* (Fruit fly)) | P15357 |
| Hypothetical 17.7 kDa protein in ABP1 (*Saccharomyces cerevisiae* (Baker's yeast)) | P37263 |
| 60S ribosomal protein L44 (*Phaffia rhodozyma* (Yeast) (*Xanthophyllomyces dendrorhous*)) | O59870 |

TABLE 1-continued

Exemplary Lysine-Rich Proteins

| Protein Name | UniProtKB/Swiss-Pro Primary Accession Number |
|---|---|
| 40S ribosomal protein S27a-2 (*Arabidopsis thaliana* (Mouse-ear cress)) | P59232 |
| 40S ribosomal protein S27a (*Neurospora crassa*) | P14799 |
| Hypothetical 9.7 kDa protein in lcnC (*Lactococcus lactis* subsp. *lactis* (*Streptococcus lactis*)) | Q00571 |
| Capsid protein C (By similarity) (Bovine viral diarrhea virus (strain CP7) (BVDV) (Mucosal disease virus)) | Q96662 |
| Hypothetical protein MJ0331 (*Methanococcus jannaschii*) | Q57777 |
| 40S ribosomal protein S27a (*Lycopersicon esculentum* (Tomato)) | P62980 |
| 40S ribosomal protein S27a (*Solanum tuberosum* (Potato)) | P62981 |
| 40S ribosomal protein S27a (*Zea mays* (Maize)) | P27923 |
| 60S ribosomal protein L44 (*Plasmodium falciparum* (isolate 3D7)) | O97231 |
| Capsid protein C (By similarity) (Bovine viral diarrhea virus (isolate NADL) (BVDV) (Mucosal disease virus)) | P19711 |
| Hypothetical protein HI0235 (*Haemophilus influenzae*) | P44588 |
| 60S ribosomal protein L44 (*Chlamydomonas reinhardtii*) | P49213 |
| 60S ribosomal protein L36a (*Brachydanio rerio* (Zebrafish) (*Danio rerio*)) | P61485 |
| 60S ribosomal protein L36a (*Fugu rubripes* (Japanese puffertish) (*Takifugu rubripes*)) | P61486 |
| 60S ribosomal protein L36a (*Ictalurus punctatus* (Channel catfish)) | P61487 |
| 30S ribosomal protein S27ae (*Sulfolobus tokodaii*) | Q975Q8 |
| 40S ribosomal protein S27a (*Dictyostelium discoideum* (Slime mold)) | P14797 |
| 50S ribosomal protein L23 (*Aquifex aeolicus*) | O66433 |
| 60S ribosomal protein L44 (*Gossypium hirsutum* (Upland cotton)) | Q96499 |
| High mobility group Protein (*Tetrahymena pyriformis*) | P40625 |
| 50S ribosomal protein L33 (*Vibrio parahaemolyticus*) | Q87T84 |
| Ribosome biogenesis protein Nop10 (*Methanococcus maripaludis*) | Q6LWK3 |
| 40S ribosomal protein S27a (*Oryza sativa* (Rice)) | P51431 |
| 60S ribosomal protein L31 (*Saccharomyces cerevisiae* (Baker's yeast)) | P14063 |
| 50S ribosomal protein L28 (*Nicotiana tabacum* (Common tobacco)) | P30956 |
| 60S ribosomal protein L38 (*Caenorhabditis elegans*) | O17570 |
| Nucleolar protein of 40 kDa (*Mus musculus* (Mouse)) | Q9ESX4 |
| Protein FAM32A-like (*Brachydanio rerio* (Zebrafish) (*Danio rerio*)) | Q6GQN4 |
| Enkurin./FTId = PRO_0000086976 (*Mus musculus* (Mouse)) | Q6SP97 |
| 60S ribosomal protein L44 (*Schizosaccharomyces pombe* (Fission yeast)) | Q9UTI8 |
| 60S ribosomal protein L36a (*Rattus norvegicus* (Rat)) | P83883 |
| 60S ribosomal protein L36a (*Sus scrofa* (Pig)) | P83884 |
| 60S ribosomal protein L36a (*Mus musculus* (Mouse)) | P83882 |
| 60S rihosomal protein L36a (*Homo sapiens* (Human)) | P83881 |
| 40S ribosomal protein S27a (*Caenorhabditis elegans*) | P37165 |
| 40S ribosomal protein S25 (*Drosophila melanogaster* (Fruit fly)) | P48588 |
| 30S ribosomal protein S27ae (*Methanococcus jannaschii*) | P54031 |
| 30S ribosomal protein S27ae (*Sulfolobus solfataricus*) | Q97ZY7 |
| 40S ribosomal protein S27a (*Hordeum vulgare* (Barley)) | P22277 |
| 50S ribosomal protein L33 (*Rhodopirellula baltica*) | Q7UMN0 |
| Capsid protein C (By similarity) (Classical swine fever virus (strain Alfort) (CSFV) (Hog cholera virus)) | P19712 |
| Small inducible cytokineB14 (*Mus musculus* (Mouse)) | Q9WUQ5 |
| Capsid protein C (By similarity) (Bovine viral diarrhea virus (strain SD-1) (BVDV) (Mucosal disease virus)) | Q01499 |
| Methanol dehydrogenase subunit 2 (*Methylobacterium extorquens*) | P14775 |
| Hypothetical protein yqbP (*Bacillus subtilis*) | P45932 |
| UPF0291 protein lmo1304 (*Listeria monocytogenes*) | Q8Y7H5 |
| 60S ribosomal protein L32 (*Saccharomyces cerevisiae* (Baker's yeast)) | P25348 |
| 60S ribosomal protein L27 (*Caenorhabditis elegans*) | P91914 |
| Nucleolar protein of 40 kDa (*Macaca fascicularis* (Crab eating macaque) (*Cynomolgus* monkey)) | Q95KF9 |
| 60S ribosomal protein L44 (*Coprinus cinereus* (Inky cap fungus)) | Q9UWE4 |
| 40S ribosomal protein S27a (*Schizosaccharomyces pombe* (Fission yeast)) | P0C016 |
| 50S ribosomal protein L35 (*Thermus thermophilus* (strain HB8/ATCC 27634/DSM 579)) | Q5SKU1 |
| 50S ribosomal protein L35 (*Thermus thermophilus*) | P80341 |
| Hypothetical 9.4 kDa protein in nrdB (*Bacteriophage T4*) | P39505 |
| Hypothetical 31.3 kDa protein in TAF145 (*Saccharomyces cerevisiae* (Baker's yeast)) | P53335 |
| 50S ribosomal protein L33 (*Vibrio vulnificus*) | Q8DDY2 |
| 50S ribosomal protein L33 (*Vibrio vulnificus* (strain YJ016)) | Q7MPS5 |
| Signal recognition particle 14 kDa (*Caenorhabditis elegans*) | O16927 |
| Endonuclease-1./FTId = PRO_0000207691 (*Buchnera aphidicola* subsp. *Acyrthosiphon pisum* (*Acyrthosiphon pisum* symbiotic bacterium)) | P57487 |
| 30S ribosomal protein S17 (Onion yellows phytoplasma) | Q6YR12 |
| Nucleolar protein of 40 kDa (*Homo sapiens* (Human)) | Q9NP64 |
| Ribosome biogenesis protein Nop10 (*Sulfolobus solfataricus*) | Q97Z78 |
| DNA topoisomerase 1 (*Rattus norvegicus* (Rat)) | Q9WUL0 |
| Probable ribosome biogenesis Protein (*Homo sapiens* (Human)) | Q9UHA3 |
| DNA topoisomerase 1 (*Mus musculus* (Mouse)) | Q04750 |

TABLE 1-continued

Exemplary Lysine-Rich Proteins

| Protein Name | UniProtKB/Swiss-Pro Primary Accession Number |
|---|---|
| Hypothetical protein aq_1894 (*Aquifex aeolicus*) | O67734 |
| DNA topoisomerase 1 (*Cricetulus griseus* (Chinese hamster)) | Q07050 |
| Zinc finger protein 273 (*Homo sapiens* (Human)) | Q14593 |
| DNA topoisomerase 1 (*Homo sapiens* (Human)) | P11387 |
| 50S ribosomal protein L28 (*Wigglesworthia glossinidia brevipalpis*) | Q8D2F1 |
| DNA topoisomerase 1 (*Cercopithecus aethiops* (Green monkey) (Grivet)) | Q7YR26 |
| RNA exonuclease 4 (*Candida glabrata* (Yeast) (*Torulopsis glabrata*)) | Q6FQA0 |
| 40S ribosomal protein S27a (*Caenorhabditis briggsae*) | P37164 |
| 30S ribosomal protein S14 (*Mycoplasma capricolum* subsp. *capricolum* (strain California kid/ATCC 27343/NCTC 10154)) | P10130 |
| 50S ribosomal protein L28 (*Clostridium perfringens*) | Q8XJM2 |
| 50S ribosomal protein L33 (*Neisseria meningitidis* serogroup A) | P66225 |
| 50S ribosomal protein L33 (*Neisseria meningitidis* serogroup B) | P66226 |
| 50S ribosomal protein L33 (*Yersinia pestis*) | Q8ZJP1 |
| 40S ribosomal protein S25 (*Ictalurus punctatus* (Channel catfish)) | Q90YP9 |
| Pleiotrophin (*Mus musculus* (Mouse)) | P63089 |
| 60S ribosomal protein L44 (*Trypanosoma brucei brucei*) | P17843 |
| 40S ribosomal protein S27a (*Manduca sexta* (Tobacco hawkmoth) (Tobacco hornworm)) | P29504 |
| 40S ribosomal protein S27a (*Lupinus albus* (White lupin)) | P47905 |
| 40S ribosomal protein S27a (*Bos taurus* (Bovine)) | P62992 |
| 40S ribosomal protein S27a (*Cavia porcellus* (Guinea pig)) | P62978 |
| 40S ribosomal protein S27a (*Homo sapiens* (Human)) | P62979 |
| 40S ribosomal protein S27a (*Plutella xylostella* (Diamondback moth)) | P68202 |
| 40S ribosomal protein S27a (*Kluyveromyces lactis* (Yeast)) | P69061 |
| 40S ribosomal protein S27a (*Gallus gallus* (Chicken)) | P79781 |
| 40S ribosomal protein S27a (*Mus musculus* (Mouse)) | P62983 |
| 40S ribosomal protein S27a (*Rattus norvegicus* (Rat)) | P62982 |
| 40S ribosomal protein S27a (*Spodoptera frugiperda* (Fall armyworm)) | P68203 |
| 60S ribosomal protein L44 (*Arabidopsis thaliana* (Mouse-ear cress)) | O23290 |
| 40S ribosomal protein S27a-1 (*Arabidopsis thaliana* (Mouse-ear cress)) | P59271 |
| 40S ribosomal protein S27a (*Ictalurus punctatus* (Channel catfish)) | P68200 |
| 40S ribosomal protein S27a (*Asparagus officinalis* (Garden asparagus)) | P31753 |
| 40S ribosomal protein S27a-3 (*Arabidopsis thaliana* (Mouse-ear cress)) | P59233 |
| 40S ribosomal protein S27a (*Drosophila melanogaster* (Fruit fly)) | P15357 |
| Hypothetical 17.7 kDa protein in ABP1 (*Saccharomyces cerevisiae* (Baker's yeast)) | P37263 |
| 60S ribosomal protein L44 (*Phaffia rhodozyma* (Yeast) (*Xanthophyllomyces dendrorhous*)) | O59870 |
| 40S ribosomal protein S27a-2 (*Arabidopsis thaliana* (Mouse-ear cress)) | P59232 |
| 40S ribosomal protein S27a (*Neurospora crassa*) | P14799 |
| Hypothetical 9.7 kDa protein in lcnC (*Lactococcus lactis* subsp. *lactis* (*Streptococcus lactis*)) | Q00571 |
| Capsid protein C (By similarity) (Bovine viral diarrhea virus (strain CP7) (BVDV) (Mucosal disease virus)) | Q96662 |
| Hypothetical protein MJ0331 (*Methanococcus jannaschii*) | Q57777 |
| 40S rihosomal protein S27a (*Lycopersicon esculentum* (Tomato)) | P62980 |
| 40S ribosomal protein S27a (*Solanum tuberosum* (Potato)) | P62981 |
| 40S ribosomal protein S27a (*Zea mays* (Maize)) | P27923 |
| 60S ribosomal protein L44 (*Plasmodium falciparum* (isolate 3D7)) | Q97231 |
| Capsid protein C (By similarity) (Bovine viral diarrhea virus (isolate NADL) (BVDV) (Mucosal disease virus)) | P19711 |
| Hypothetical protein HI0235 (*Haemophilus influenzae*) | P44588 |
| 60S ribosomal protein L44 (*Chlamydomonas reinhardtii*) | P49213 |
| 60S ribosomal protein L36a (*Brachydanio rerio* (Zebrafish) (*Danio rerio*)) | P61485 |
| 60S ribosomal protein L36a (*Fugu rubripes* (Japanese pufferfish) (*Takifugu rubripes*)) | P61486 |
| 60S ribosomal protein L36a (*Ictalurus punctatus* (Channel catfish)) | P61487 |
| 30S ribosomal protein S27ae (*Sulfolobus tokodaii*) | Q975Q8 |
| 40S ribosomal protein S27a (*Dictyostelium discoideum* (Slime mold)) | P14797 |
| 50S ribosomal protein L23 (*Aquifex aeolicus*) | O66433 |
| 60S ribosomal protein L44 (*Gossypium hirsutum* (Upland cotton)) | Q96499 |
| High mobility group Protein (*Tetrahymena pyriformis*) | P40625 |

A particular amino acid-rich peptide or a protein may be cloned into an expression vector and introduced into a suitable host cell. Alternatively, a recombinantly engineered protein that has a chosen amino acid profile may be cloned into an expression vector and introduced into a suitable host cell (e.g., microorganism). The recombinantly-engineered proteins may have an enhanced content of one or more of the essential amino acids, or the proteins may have an enhanced content of one or more of the other limiting amino acids for milk production, which may include lysine, methionine, phenylalanine, threonine, isoleucine, and tryptophan. As such, the recombinantly-engineered proteins may be designed to include a selected profile of amino acids. The ratios of the amino acids in the recombinantly-engineered proteins may be varied or designed to match the ratios that are predicted to be optimal for dairy cattle based on feeding studies or predictions. In one embodiment, the selected profile of amino acids, e.g., in a recombinantly produced protein, is similar to the profile of blood meal. After a protein has been designed and its gene has been cloned into an expression vector, the protein may be expressed (or overexpressed) in a microbial host such as E. coli. Corynebacterium, Brevibacterium, Bacillus, Yeast, etc.

In order to optimize the expression of the peptide or protein in the host, the sequence of the peptide or protein may be selected to utilize specific tRNAs that are prevalent in the host. Alternatively, selected tRNAs may be coexpressed in the host to facilitate expression of the peptide or protein. Alternatively, single and multiple codon usage patterns can be adjusted for optimal yield, folding, and localization. The recombinantly-engineered peptide or proteins may include specific sequences to facilitate purification of the peptide or proteins. The proteins may also include "leader sequences" that target the protein to specific locations in the host cell such as the periplasm, or to target the protein for secretion. The recombinantly-engineered peptide or proteins may also include protease cleavage sites to facilitate cleavage of the proteins in the abomasum and enhance delivery of amino acids in the peptide or protein to the small intestine. For example, one such protease is pepsin, one of the protein-digesting enzymes of the abomasum in cattle. Pepsin demonstrates a preferential cleavage of peptides at hydrophobic preferentially aromatic, residues in the P1 and P1' positions. In particular, pepsin cleaves proteins on the carboxy side of phenylalanine, tryptophan, tyrosine, and leucine. More favorably, the polypeptide is readily cleavable by animal proteases generally.

In some embodiments of the invention, a microorganism is modified in such a way that the modified microorganism is enriched in vitamins. The vitamins include but are not limited to, vitamin A (retinol), vitamin B1 (thiamine), vitamin B2 (riboflavin), vitamin B3 (Niacin), vitamin B5 (Pantothenic acid), vitamin B6 (Pyridoxine), vitamin B7 (Biotin), vitamin B9 (Folic acid), vitamin B12 (cyanocobalamin), vitamin $C^{[3]}$ (ascorbic acid), vitamin D1-D4 (lamisterol, ergocalciferol, calciferol, dihydrotachysterol, 7-dehydrositosterol), vitamin E (tocopherol), and vitamin K (naphthoquinone).

Different organisms need different trace organic substances. Most mammals need, with few exceptions, the same vitamins as humans. One exception is vitamin C, which can be synthesized by all other mammals except other higher primates and guinea pigs. The less related a species is to mammals, the more different the organisms' requirements may become.

The present invention includes methods of producing vitamins in modified microorganisms by any means as the starting material. The present invention includes various aspects of biological materials and intermediates useful in the biological production of vitamins. For example, vitamin E (d-α-tocopherol) is an important nutritional supplement in humans and animals. The α-tocopherol, tocopherol and α-tocopheryl esters can be produced from framesol or geranylgeraniol (GG). Framesol can be used as a starting material to chemically synthesize the final product, α-tocopheryl esters. Alternatively, the framesol can be converted chemically to GG. GG produced biologically or by synthesis from framesol, can then be used as a starting material to make α-tocopheryl and α-tocopheryl esters. Farnesol and GG are prenyl alcohols produced by dephosphorylation of farnesylpryrophosphate (FPP) and geranylgeranylpyrophosphate (GGPP), respectively. FPP and GGPP are intermediates in the biosynthesis of isoprenoid compounds, including sterols, ubiquinones, heme, dolichols, and carotenoids, and are used in the post-translational prenylation of proteins. Both FPP and GGPP are derived from isopentylpyrophosphate (IPP). Millis et al. U.S. Pat. No. 6,410,755, is incorporated herein by reference in its entirety.

Isoprenoids are the largest family of natural products, with about 22,000 different structures known. All isoprenoids are derived from the $C_5$ compound IPP. Thus, the carbon skeletons of all isoprenoid compounds are created by sequential additions of the $C_5$ units to the growing polyprenoid chain. The two different pathways leading to IPP exist. Fungi (such as yeast) and animals possess mevalonate-dependent pathway which may use acetyl CoA as the initial precursor. Bacteria and higher plants, on the other hand, may possess a mevalonate independent pathway, also referred to as the non-mevalonate pathway, leading from pyruvate and glyceraldehyde 3-phosphate.

Embodiments of the present invention include the biological production of vitamins or any starting material or intermediate for the production of vitamins, in prokaryotic or eukaryotic cell cultures and cell-free systems, irrespective of which pathway the organism utilizes. For example, the biosynthesis of the precursor of all isoprenoids, IPP utilizes the mevalonate-dependent or independent pathway. Preferably the cells used in the cell culture are genetically modified to increase the yield of vitamins or intermediate or a starting material therefor. Cells may be genetically modified by genetic engineering techniques (i.e., recombinant technology), classical microbiological techniques, or a combination of such techniques and can also include naturally occurring genetic variants.

Embodiments of the present invention include biological production of framesol or GG by culturing a microorganism, preferably yeast, which has been genetically modified to modulate the activity of one or more of the enzymes in its isoprenoid biosynthetic pathway, to decrease (including eliminating) the action of squalene synthase activity, to increase the action of HMG-CoA reductases, to increase the action of GGPP synthase, to increase the action of FPP synthase, or to increase phosphatase action to increase conversion of FPP to framesol or GGPP to GG.

A particular amino acid, peptide or protein having an enhanced content of amino acid may be at least partially purified from the fermentation broth or lysed biomass. For example, lysine or lysine-rich proteins may be isolated based on the isoelectric point of lysine. Similarly, the presence of the lysine in a lysine-rich protein may be used to isolate the protein, based on the isoelectric point of the protein. The desired isoelectric point for a particular amino acid-rich protein may be varied by using recombinant technology to alter the amino acid composition of the protein (e.g., to create a protein having a selected lysine content).

The unique isoelectric point (pI) of a particular amino acid compared to other amino acids may permit selective precipitation of that amino acid, preferential extraction into organic solvents, and binding to various ion exchange resin or metal chelation matrices. A particular amino acid or a peptide may bind to transition metals such as nickel (Ni) and may be used to facilitate isolation of the protein (e.g., by binding, the protein to a nickel-containing matrix). Other transition metals may be used, such as copper (Cu). In addition, a size of the amino acid may permit the use of unique combinations of size exclusion chromatography and ion-exchange resins to isolate that amino acid from fermentation broth containing other amino acids and co-products. Additionally, the unique pI of an amino acid could result in specific and unique pI values for that amino acid-rich protein thus permitting selective precipitation of these proteins from other cellular proteins for subsequent use in feed or food.

Essential and Non-Essential Amino Acids

The modified microorganisms of the present invention can be modified to produce high levels of nutrients including essential and non-essential amino acids. The complete feed or the fermentation residuals containing such modified microorganisms contain high levels of nutrients including essential and non-essential amino acids.

An essential amino acid for an organism is an amino acid that cannot be synthesized by the organism from other available resources, and therefore must be supplied as part of its diet. Eight amino acids are generally regarded as essential for humans: lysine, methionine, phenylalanine, threonine, isoleucine, tryptophan, valine, and leucine. Two others, histidine and arginine may be essential in children and possibly in seniors. Taurine may be necessary to preserve arterial and collagen pliability. The essential amino acids vary from species to species, as different metabolisms are able to synthesize different substances. For instance, taurine is essential for cats, but may not be for dogs. Some amino acids can be produced from others. The sulfur-containing amino acids, methionine and homocysteine, can be converted into each other but neither can be synthesized de novo in humans. Likewise, cysteine can be made from homocysteine, but not de novo. Sulfur-containing amino acids can be considered a single pool of nutritionally-equivalent amino acids. Likewise, arginine, ornithine, and citrulline, which are interconvertible by the urea cycle, can be considered a single pool.

Essential amino acids for cats include: arginine, histidine, isoleucine, leucine, lysine, methionine, phenylalanine, threonine, tryptophan, valine, and taurine. Taurine is an amino acid that is necessary for proper bile formation, eye health, and proper function of the heart. Cats require a high amount of taurine for their body functions, yet have limited enzymes that can produce taurine from other amino acids such as methionine and cysteine. Therefore, they need a diet high in taurine. If taurine is deficient, signs such as a heart condition called dilated cardiomyopathy, retinal degeneration, reproductive failure, and abnormal kitten development can occur. Most animals may manufacture the amino acid ornithine through various processes, some of which may require arginine. In cats, the method to produce ornithine is to convert it from arginine. If cats are deficient in arginine, there may not have enough ornithine to bind the ammonia, and severe signs such as salivation, vocalization, ataxia, and even death can result from the high ammonia levels. These signs often occur several hours after a meal, when most of the ammonia is produced. The complete feed with high nutritional content as in the present invention can help treat or alleviate these disorders in animals.

A balanced nutritional diet for a variety of domestic animals is known in the art. Committee on Animal Nutrition, National Research Council has published numerous guidelines to facilitate those skilled in the art to formulate a balanced animal feed. See for example, Nutrient Requirements of Beef Cattle: 7$^{th}$ Revised Edition (2000, ISBN 0309069343), Nutritional Requirements of Swine: 10$^{th}$ Revised Edition (1998, ISBN 0309059933), and Nutritional Requirements of Dairy Cattle: 7$^{th}$ Revised Edition (2001, ISBN 0309069971), all of which are incorporated herein by reference in their entirety.

Fermentation Media and Conditions

The modified microorganism as discussed above may be cultured in a fermentation medium for production of nutrients. An appropriate, or effective, fermentation medium refers to any medium in which a modified microorganism of the present invention, when cultured, is capable of producing nutrients. Such a medium is typically an aqueous medium comprising assimilable carbon, nitrogen and phosphate sources. Such a medium can also include appropriate salts, minerals, metals, and other nutrients. It should be recognized, however, that a variety of fermentation conditions are suitable and can be selected by those skilled in the art.

Sources of assimilable carbon which can be used in a suitable fermentation medium include, but are not limited to, sugars and their polymers, including, dextrin, sucrose, maltose, lactose, glucose, fructose, mannose, sorbose, arabinose and xylose; fatty acids; organic acids such as acetate; primary alcohols such as ethanol and n-propanol; and polyalcohols such as glycerine. Preferred carbon sources in the present invention include monosaccharides, disaccharides, and trisaccharides. The most preferred carbon source is glucose.

The concentration of a carbon source, such as glucose, in the fermentation medium should promote cell growth, but not be so high as to repress growth of the microorganism used. Typically, fermentations are run with a carbon source, such as glucose, being added at levels to achieve the desired level of growth and biomass. In other embodiments, the concentration of a carbon source, such as glucose, in the fermentation medium is greater than about 1 g/L, preferably greater than about 2 g/L, and more preferably greater than about 5 g/L. In addition, the concentration of a carbon source, such as glucose, in the fermentation medium may be less than about 100 g/L, less than about 50 g/L, or less than about 20 g/L. It should be noted that references to fermentation component concentrations can refer to both initial and/or ongoing component concentrations. In some cases, it may be desirable to allow the fermentation medium to become depleted of a carbon source during fermentation.

Sources of assimilable nitrogen that can be used in a suitable fermentation medium include, but are not limited to, simple nitrogen sources, organic nitrogen sources, and complex nitrogen sources. Such nitrogen sources include anhydrous ammonia, ammonium salts, and substances of animal, vegetable, and/or microbial origin. Suitable nitrogen sources include, but are not limited to, protein hydrolysates, microbial biomass hydrolysates, peptone, yeast extract, ammonium sulfate, urea, and amino acids. Hydrolyzed grain products form a suitable nitrogen source. Typically, the concentration of the nitrogen sources, in the fermentation medium can be greater than about 0.1 g/L, greater than about 0.25 g/L, or greater than about 1.0 g/L. Beyond certain concentrations, however, the addition of a nitrogen source to the fermentation medium is not advantageous for the growth of the microorganisms. As a result, the concentration of the nitrogen sources, in the fermentation medium may be less than about 20 g/L, less than about 10 g/L or less than about 5 g/L. Further, in some instances it may be desirable to allow the fermentation medium to become depleted of the nitrogen sources during fermentation.

The effective fermentation medium can contain other compounds such as inorganic salts, vitamins, trace metals, or growth promoters. Such other compounds can also be present in carbon, nitrogen or mineral sources in the effective medium or can be added specifically to the medium.

The fermentation medium can also contain a suitable phosphate source. Such phosphate sources include both inorganic and organic phosphate sources. Preferred phosphate sources include, but are not limited to, phosphate salts such as mono or dibasic sodium and potassium phosphates, ammonium phosphate and mixtures thereof. Typically, the concentration of phosphate in the fermentation medium is greater than about 1.0 g/L, preferably greater than about 2.0 g/L and more preferably greater than about 5.0 g/L. Beyond certain concentrations, however, the addition of phosphate to the fermentation medium is not advantageous for the growth of the microorganisms. Accordingly, the concentration of phosphate in the fermentation medium is typically less than about 20 g/L, preferably less than about 15 g/L, and more preferably less than about 10 g/L.

A suitable fermentation medium can also include a source of magnesium, preferably in the form of a physiologically acceptable salt, such as magnesium sulfate heptahydrate, although other magnesium sources in concentrations that contribute similar amounts of magnesium can be used. Typically, the concentration of magnesium in the fermentation medium is greater than about 0.5 g/L, preferably greater than about 1.0 g/L, and more preferably greater than about 2.0 g/L. Beyond certain concentrations, however, the addition of magnesium to the fermentation medium is not advantageous for the growth of the microorganisms. Accordingly, the concentration of magnesium in the fermentation medium is typically less than about 10 g/L, preferably less than about 5 g/L, and more preferably less than about 3 g/L. Further, in some instances it may be desirable to allow the fermentation medium to become depleted of a magnesium source during fermentation.

The fermentation medium can also include a biologically acceptable chelating agent, such as the dihydrate of trisodium citrate. In such instance, the concentration of a chelating agent in the fermentation medium is greater than about 0.2 g/L, preferably greater than about 0.5 g/L, and more preferably greater than about 1 g/L. Beyond certain concentrations, however, the addition of a chelating agent to the fermentation medium is not advantageous for the growth of the microorganisms. Accordingly, the concentration of a chelating agent in the fermentation medium is typically less than about 10 g/L, preferably less than about 5 g/L, and more preferably less than about 2 g/L.

The fermentation medium can also initially include a biologically acceptable acid or base to maintain the desired pH of the fermentation medium. Biologically acceptable acids include, but are not limited to, hydrochloric acid, sulfuric acid, nitric acid, phosphoric acid and mixtures thereof. Biologically acceptable bases include, but are not limited to, ammonium hydroxide, sodium hydroxide, potassium hydroxide and mixtures thereof.

The fermentation medium can also include a biologically acceptable calcium source, including, but not limited to, calcium chloride. Typically, the concentration of the calcium source, such as calcium chloride, dihydrate, in the fermentation medium is within the range of from about 5 mg/L to about 2000 mg/L, preferably within the range of from about 20 mg/L to about 1000 mg/L, and more preferably in the range of from about 50 mg/L to about 500 mg/L.

The fermentation medium can also include sodium chloride. Typically, the concentration of sodium chloride in the fermentation medium is within the range of from about 0.1 g/L to about 5 g/L, preferably within the range of from about 1 g/L to about 4 g/L, and more preferably in the range of from about 2 g/L to about 4 g/L.

The fermentation medium can also include trace metals. Such trace metals can be added to the fermentation medium as a stock solution that, for convenience, can be prepared separately from the rest of the fermentation medium. Typically, the amount of such a trace metals solution added to the fermentation medium is greater than about 1 mil/L, preferably greater than about 5 ml/L, and more preferably greater than about 10 ml/L. Beyond certain concentrations, however, the addition of a trace metals to the fermentation medium is not advantageous for the growth of the microorganisms. Accordingly, the amount of such a trace metals solution added to the fermentation medium is typically less than about 100 ml/L, preferably less than about 50 ml/L, and more preferably less than about 30 ml/L. It should be noted that, in addition to adding trace metals in a stock solution, the individual components can be added separately, each within ranges corresponding independently to the amounts of the components dictated by the above ranges of the trace metals solution.

A suitable trace metals solution can include, but is not limited to sodium selenate; ferrous sulfate; heptahydrate; cupric sulfate, pentahydrate; zinc sulfate, heptahydrate; sodium molybdate, dihydrate; cobaltous chloride; Selenium or chromium solution; hexahydrate; and manganous sulfate monohydrate. Hydrochloric acid may be added to the stock solution to keep the trace metal salts in solution.

The fermentation medium can also include vitamins. Such vitamins can be added to the fermentation medium as a stock solution that, for convenience, can be prepared separately from the rest of the fermentation medium, Typically, the amount of such vitamin solution added to the fermentation medium is greater than 1 ml/L, preferably greater than 5 mL and more preferably greater than 10 ml/L. Beyond certain concentrations, however, the addition of vitamins to the fermentation medium is not advantageous for the growth of the microorganisms. Accordingly, the amount of such a vitamin solution added to the fermentation medium is typically less than about 50 ml/L, preferably less than 30 ml/L and more preferably less than 20 ml/L. It should be noted that, in addition to adding vitamins in a stock solution, the individual components can be added separately each within the ranges corresponding independently to the amounts of the components dictated by the above ranges of the vitamin stock solution. A suitable vitamin solution can include, but is not limited to, biotin, calcium pantothenate, inositol, pyridoxine-HCl and thiamine-HCl.

The fermentation medium can also include sterols. Such sterols can be added to the fermentation medium as a stock solution that is prepared separately from the rest of the fermentation medium. Sterol stock solutions can be prepared using a detergent to aid in solubilization of the sterol. Typically, an amount of sterol stock solution is added to the fermentation medium such that the final concentration of the sterol in the fermentation medium is within the range of from about 1 mg/L to 3000 mg/L, preferably within the range from about 2 mg/L to 2000 mg/L, and more preferably within the range from about 5 mg/L to 2000 mg/L.

Microorganisms of the present invention can be cultured in conventional fermentation modes, which include, but are not limited to, batch, fed-batch, cell recycle, and continuous. In a fed-batch mode, when during fermentation some of the components of the medium are depleted, it may be possible to initiate the fermentation with relatively high concentrations of such components so that growth is supported for a period of time before additions are required. The preferred ranges of these components are maintained throughout the fermentation by making additions as levels are depleted by fermentation. Levels of components in the fermentation medium can be monitored by, for example, sampling the fermentation medium periodically and assaying for concentrations. Alternatively, once a standard fermentation procedure is developed, additions can be made at timed intervals corresponding to known levels at particular times throughout the fermentation. The additions to the fermentor may be made under the control of a computer in response to fermentor conditions or by a preprogrammed schedule. Moreover, to avoid introduction of foreign microorganisms into the fermentation medium, addition is performed using aseptic addition methods, as are known in the art. In addition, a small amount of anti-foaming agent may be added during the fermentation, or anti-foaming device may be employed.

The temperature of the fermentation medium can be any temperature suitable for growth and production of the nutrients of the present invention. For example, prior to inoculation of the fermentation medium with an inoculum, the fermentation medium can be brought to and maintained at a temperature in the range of from about 20° C. to about 45° C., preferably to a temperature in the range of from about 25° C. to about 40° C., and more preferably in the range of from about 28° C. to about 32° C.

The pH of the fermentation medium can be controlled by the addition of acid or base to the fermentation medium. In such cases when ammonia is used to control pH, it also conveniently serves as a nitrogen source in the fermentation medium. Preferably, the pH is maintained from about 3.0 to about 8.0, more preferably from about 3.5 to about 7.0, and most preferably from about 4.0 to about 6.5.

The fermentation medium can also be maintained to have a dissolved oxygen content during the course of fermentation to maintain cell growth and to maintain cell metabolism for production of the nutrients. The oxygen concentration of the fermentation medium can be monitored using known methods, such as through the use of an oxygen electrode. Oxygen can be added to the fermentation medium using methods known in the art, for, through agitation and aeration of the medium by stirring, shaking or sparging. Preferably, the oxygen concentration in an aerobic fermentation medium can be in the range of from about 20% to about 100% of the saturation value of oxygen in the medium based upon the solubility of oxygen in the fermentation medium at atmospheric pressure and at a temperature in the range of from about 20° C. to about 40° C. Periodic drops in the oxygen concentration below this range may occur during fermentation, however, without adversely affecting the fermentation.

Although aeration of the medium has been described herein in relation to the use of air, other sources of oxygen can be used. Particularly useful is the use of an aerating gas that contains a volume fraction of oxygen greater than the volume fraction of oxygen in ambient air. In addition, such aerating gases can include other gases which do not negatively affect the fermentation. In some embodiments, fermentation is performed under conditions well established in the art.

The fermentation medium can be inoculated with an actively growing culture of microorganisms of the present invention in an amount sufficient to produce, after a reasonable growth period, a high cell density. Typical inoculation cell densities are within the range of from about 0.01 g/L to about 10 g/L, preferably from about 0.2 g/L to about 5 g/L and more preferably from about 0.05 g/L to about 1.0 g/L, based on the dry weight of the cells. In production scale fermentors, however, greater inoculum cell densities are preferred. The cells are then grown to a cell density in the range of from about 10 g/L to about 100 g/L preferably from about 20 g/L to about 80 g/L, and more preferably from about 50 g/L to about 70 g/L. The residence times for the microorganisms to reach the desired cell densities during fermentation are typically less than about 200 hours, preferably less than about 120 hours, and more preferably less than about 96 hours.

In one mode of operation of the present invention, the carbon source concentration, such as the glucose concentration, of the fermentation medium is monitored during fermentation. Glucose concentration of the fermentation medium can be monitored using known techniques, such as, for example, use of the glucose oxidase enzyme test or high pressure liquid chromatography, which can be used to monitor glucose concentration in the supernatant, e.g., a cell-free component of the fermentation medium. As stated previously, the carbon source concentration should be kept below the level at which cell growth inhibition occurs. Although such concentration may vary from organism to organism, typically for glucose as a carbon source, cell growth inhibition may occur at glucose concentrations greater than at about 60 g/L, and can be determined readily by trial. The glucose concentration in the fermentation medium is maintained in the range of from about 1 g/L to about 100 g/L, more preferably in the range of from about 2 g/L to about 50 g/L, and yet more preferably in the range of from about 5 g/L to about 20 g/L. Although the carbon source concentration can be maintained within desired levels by addition of, for example, a substantially pure glucose solution, it is acceptable, and may be preferred, to maintain the carbon source concentration of the fermentation medium by addition of aliquots of the original fermentation medium. The use of aliquots of the original fermentation medium may be desirable because the concentrations of other nutrients in the medium (e.g. the nitrogen and phosphate sources) can be maintained simultaneously. Likewise, the trace metals concentrations can be maintained in the fermentation medium by addition of aliquots of the trace metals solution.

Coating and Structural Modification of the Nutrients

The nutritionally enriched modified microorganism may be further treated to facilitate rumen bypass. The peptide or protein must escape ruminal degradation and pass to the small intestine to supply sufficient amounts of amino acids. The primary methods developed to prevent fermentative digestion of amino acids include (1) coating a product that has an enhanced amino acid content with a composition that protects the product from degradation in the rumen and/or (2) structural manipulation of the amino acid to produce amino-acid analogs that demonstrate reduced degradation in the rumen.

Proteins with significant secondary or tertiary structure (e.g., di-sulfide bonds) may display better rumen protection. In addition to providing a source of essential amino acids for ruminant feed, an essential amino acid-rich protein may closely resemble the "essential amino acid-rich" proteins that are present in blood meal. For example, blood meal may include the porcine hemoglobin alpha chain. By way of example only, an essential amino acid-rich peptide or protein in a modified microorganism may be coated with polymeric compounds, or polymerized, protein, fat, mixtures of fat and calcium, mixtures of fat and protein, and with metal salts of long chain fatty acids. The essential amino acid-rich peptide or protein may also be coated with pH-sensitive polymers. A pH-sensitive polymer is stable at ruminal pH, but breaks down when it is exposed to abomasal pH, releasing the peptide or protein for digesting in the abomasums and absorption in the small intestine. As such, free amino acids may be coated to provide protection from degradation in the rumen. The essential amino acid or an essential amino acid-rich peptide or protein may be reacted with one or more reducing carbohydrates (e.g., xylose, lactose, glucose, and the like).

The nutrients may be coated with a variety of coating materials. For example, vegetable oils (such as soy bean oil), a mixture of a hydrophobic, high melting point compound and a lipid. The combination of one or more, hydrophobic, high melting point compounds (e.g., mineral salts of fatty acids, such as commercial grade zinc stearate) with one or more type of lipid forms a coating material that can protect the content and functionality of the coated ingredient(s). These coatings can be formulated to meet the needs of high temperature and pressure processing conditions as well as protection of the amino acid payload from the microbial environment of the rumen. Suitable coatings are described in U.S. Patent Publication No. 2003/0148013, which is incorporated herein by reference in its entirety. Hydrophobic, high melting point compounds typically have a melting point of at least about 70° C., and more desirably, greater than 100° C. In particular, zinc salts of fatty acids, which have a melting point between about 115° C. and 130° C., are suitable hydrophobic, high melting point compounds.

The lipid component typically has a melting point of at least about 0° C. and more suitably no less than about 40° C. The lipid component may include vegetable oil, such as soybean oil. In other embodiments, the lipid component may be a triacylglycerol with a melting point of about 45-75° C. Commercial grade stearic acid may be selected as a representative lipid from a group including but not limited to: stearic acid, hydrogenated animal fat, animal fat (e.g., animal tallow), vegetable oil, (such as crude vegetable oil and/or hydrogenated vegetable oil, either partially or fully hydrogenated), lecithin, palmitic acid, animal oils, wax, fatty acid esters ($C_8$ to $C_{24}$), fatty acids ($C_8$ to $C_{24}$). The coating may be present in the coated product in an amount from 1-2000 wt. %, relative to the weight of the coated ingredient. Commonly, the coating represents about 15 to 85 wt. %, relative to the weight of the coated ingredient. More commonly, the coating represents about 20 to 60 wt. % and/or 30 to 40 wt. %, relative to the weight of the coated ingredient. The coating may be prepared from a hydrophobic mixture. The coating may include a surfactant.

The coating may use one or more, hydrophobic, insoluble compounds combined with a lipid. For example, commercial grade zinc stearate is extremely hydrophobic and completely insoluble in water. The addition of commercial grade zinc stearate to the coating formula may improve the protection level of the ingredient and its functionality, significantly as compared to a lipid only coating. For example, by combining zinc stearate with a somewhat insoluble lipid such as commercial grade stearic acid, the coating compound may provide better protection from leaching (i.e., loss of the active ingredient from the coated product), when the coated product is in an aqueous medium. As such, the benefit of the present coating composition may be utilized in feeds designed for ruminants to bypass the rumen and deliver the active ingredient to the small intestine.

In addition to facilitating rumen bypass, the coating may also be useful for protecting the coated nutrients against heat and pressure experienced during the manufacturing process (pelleting and extrusion). The coating composition may be useful in all types of production processes where heat is applied and heat susceptible ingredients are used. Ingredients which may benefit from this form of protection are ingredients that are subject to heat damage or degradation, such as amino acids, proteins, enzymes, vitamins, pigments, and attractants. In addition to protecting ingredients from heat related damage or loss there is also the need to protect ingredients to damage or loss attributable to association or chemical reaction with other ingredients. The method of encapsulation may prevent harmful association, or reactions with other ingredients, or oxidation. As such, the method of encapsulation provides the ability to prepackage or combine ingredients in a formulation, where the ingredients would be usually packaged individually.

The coating composition may be prepared in a number of ways. Preferably, the preparation process includes making a solid solution of the zinc organic salt component and the lipid component. In one embodiment, the zinc organic salt and the lipid component may be melted until they both dissolve and form a solution. The solution may then be allowed to solidify to form a solid solution. In addition to the zinc organic acid component and the lipid component, the coating may include other ingredients. For example, the coating may include an one or more emulsifying agents such as glycerin, polysaccharides, lecithin, gelling agents, and soaps, which may improve the speed and effectiveness of the encapsulation process. Additionally, the coating may include an anti-oxidant to provide improved protection against oxidation effects. Further, the coating composition may include other components that may or may not dissolve in the process of forming the solid solution. For example, the coating composition may include small amounts of zinc oxide and other elements or compounds.

A suitable coating may be prepared from a partially hydrogenated vegetable oil such as soybean oil. Other suitable vegetable oils, which be at least partially hydrogenated, include palm oil, cottonseed oil, corn oil, peanut oil, palm kernel oil, babassu oil, sunflower oil, safflower oil, and mixtures thereof. A suitable coating may be prepared from a mixture that includes a partially hydrogenated vegetable oil and additional constituents, such as a wax. Suitable waxes include beeswax, petroleum wax, rice bran wax, castor wax, microcrystalline wax, and mixtures thereof. In some embodiments, a suitable coating is prepared from a mixture that includes about 85-95% partially hydrogenated vegetable oil (preferably about 90%) and about 5-15% wax (preferably about 10%). The coating may include an agent for modifying the density of the coated substrate, for example, a surfactant, such as polysorbate 60, polysorbate 80, propylene glycol, sodium dioctylsulfocsuccinate, sodium lauryl sulfate, lactylic esters of fatty acids, polyglycerol esters of fatty acids, and mixtures thereof.

A coated substrate (or pre-coated substrate) may be prepared by spraying a hydrophobic mixture that includes a partially hydrogenated vegetable oil (85%-95%) and a wax (5%-15%) on a substrate that include L-His and/or a histidine rich protein. Optionally, a pre-coated substrate may be further coated by spraying the surface of the pre-coated substrate with a surfactant to form the coated substrate. The coated substrate may have the following composition: substrate (40-80%); hydrophobic mixture (20-60%); surfactant (0-40%) (optional). The coated substrate may have a specific gravity of about 0.3-2.0 (more suitably about 1.3-1.5). In one embodiment, the coated substrate includes: about 50% substrate; about 35% hydrophobic mixture; and about 15% surfactant. The coated substrate may be prepared by pre-coating the substrate with a hydrophobic mixture, and subsequently coating the pre-coated substrate with a surfactant.

After the coating composition is prepared, it can then be used to prepare the protected nutrient. One suitable procedure for preparing the protected ingredient uses encapsulation technology, preferably microencapsulation technology. Microencapsulation is a process by which tiny amounts of gas, liquid, or solid ingredients are enclosed or surrounded by a second material, in this case a coating composition, to shield the ingredient from the surrounding environment. A number of microencapsulation processes could be used to prepare the protected ingredient such as spinning disk, spraying, co-extrusion, and other chemical methods such as complex coacervation, phase separation, and gelation. One suitable method of microencapsulation is the spinning disk method. In the spinning disk method, an emulsion and/or suspension of the active-ingredient and the coating composition is prepare and gravity-fed to the surface of a heated rotating disk. As the disk rotates, the emulsion/suspension spreads across the surface of the disk to form a thin layer because of centrifugal forces. At the edge of the disk, the emulsion/suspension is sheared into discrete droplets in which the active ingredient is surrounded by the coating. As the droplets fall from the disk to a collection hopper, the droplets cool to form a microencapsulated ingredient (i.e., a coated product). Because the emulsion or suspension is not extruded through orifices, this technique permits use of a higher viscosity coating and allows higher loading of the ingredient in the coating. The encapsulation of ingredients for use in animal feeds is described in U.S. Patent Publication No. 2003/0148013, which is incorporated herein by reference in its entirety.

Amino acids (such as histidine) and/or proteins (such as histidine-rich proteins) may also be chemically altered to protect the amino acid in the rumen and to increase the supply of specific amino acids provided to the abomasums and small intestine. For example, methionine hydroxyl analog (MHA) has been used as an amino acid supplement. In addition, amino acids may be provided as amino acid/mineral chelates. Zinc-methionine and zinc-lysine complexes have been used as amino acid supplements.

Amino Acid Requirement

In diet formulation for a mammal, a predicted digestible microbial amino acid contribution from rumen fermentation is subtracted from the animal's amino acid requirements, as determined by the animal's profile. The amount of amino acids that need to be supplied as undegradable essential amino acid (UEAA) from feed is the difference between the animal's amino acid requirements and the amino acids supplied from digestible microbial amino acids. The amino acid profile of milk can be compared to the profile of amino acids produced by modified-microorganisms within the digestive tract of the animal (i.e., microbial amino acid profile). Differences between the microbial and milk amino acid profiles indicate amino acids that may be in excess or limiting. However, this amino acid profile comparison provides only part of the needed information in order to increase production of a chosen animal product. The efficiency with which the body incorporates amino acids in the small intestine into a chosen animal product may also be considered. By determining the output/input amino acid profile ratio and by determining the efficiency of incorporation, dairy digestible amino acid requirements may be determined. It has been established that histidine, lysine, methionine, phenylalanine, and threonine are likely to be limiting amino acids for milk production in dairy cows. A similar determination may be performed for the amino acid profile of muscle.

Amino acids required in feeds for dairy cows are called Dairy Digestible Amino Acids ("ddAA"). The sum of the digestible microbial amino acid plus the digestible rumen undegraded essential amino acid (UEAA) concentration of that same amino acid is the ddAA. Dairy Digestible Amino Acids represent the supply of total digestible AA to the small intestine. The total amino acid requirements of a dairy animal may be determined as follows. The total amount of an amino acid required ("TAAR") is equal to the amount required for maintenance ("Maintenance Amino Acid" or "MAA") plus the amount of the amino acid required for milk production ("Milk Amino Acid Output" or "MAAO") plus the amount of the amino acid required for growth ("Growth Amino Acid" or "GAA") (i.e., TAAR=MAA+MAAO+GAA).

Limiting amino acids may be supplied to an animal to increase production of a chosen animal product (e.g., milk) by supplementing the animal's feed with the limiting amino acid. Limiting amino acids may be identified by analyzing the amino acid profile of the chosen animal product (i.e., output profile) and comparing this profile to the profile of amino acids supplied to the animal (i.e., input profile). Methods for determining amino acid requirements are known in the art and are described in U.S. Pat. No. 5,145,695 and U.S. Pat. No. 5,219,596, which are incorporated by reference herein in their entireties. For example, the amino acid profile of milk can be compared to the profile of amino acids produced by microbes within the digestive tract of the animal (i.e., microbial amino acid profile). Differences between the microbial and milk amino acid profiles indicate where amino acids may be in excess or limiting.

Business Methods

The present invention provides business methods to develop and evaluate processes and products to increase the value of corn-to-ethanol co-products, such as distillers dried grains. It is achieved by using modified microorganisms to improve the nutritional content of these coproducts formed in ethanol production to form nutrient enriched animal feed and other value-added products, thus increasing ethanol production economics. Ethanol industry represents the third largest market for U.S. corn. Fuel ethanol production is an integral part of rural economic development, environmental improvement, and gasoline marketing. The business method of the invention provides valuable co-products in the form of nutritionally enriched complete feed which would add significant commercial value to the ethanol fermentation industry.

Agricultural and rural economies have been suffering from the effects of low commodity prices. Generally speaking, the price for many agricultural commodities received by the farmer has been below the cost of production. This situation has caused many farmers to go out of business that, in turn, has caused many rural economies to collapse. Furthermore, the energy security of the United States has become unstable because the U.S. increasingly imports large quantities of oil. Additionally, the U.S. economy suffers when the availability, and thus the cost, of imported oil dramatically fluctuates. The complete feed of the present invention helps to establish value-added co-products obtained from ethanol production, which would help support the development of the domestic bioethanol industry, provide increased and sustainable incomes in rural economies, develop new bio-based products that will replace products currently made from petroleum, and increase the domestic production of renewable energy that, in turn, can improve the energy security of the U.S. The consumer and general public may benefit from the present invention through the stabilization of fuel availability as well as price of gasoline at the pump. Since the nutritionally enriched complete feed is made from raw agricultural commodities, the present invention would also improve rural and agricultural economies, and preserve air and water quality.

One aspect of the invention relates to a business method of increasing value output of a fermentation plant, by performing a fermentation reaction with the use of a modified microorganism; and marketing or selling one or more of the products of the fermentation reaction comprising the modified microorganism. The microorganism is modified in such a way that the modified microorganism is enhanced in nutritional content. The modified microorganism are enriched in nutrients such as, by way of example only, fats, fatty acids, lipids such as phospholipid, vitamins, essential amino acids, peptides, proteins, carbohydrates, sterols, enzymes, and trace minerals such as, iron, copper, zinc, manganese, cobalt, iodine, selenium, molybdenum, nickel, fluorine, vanadium, tin and silicon. Another aspect of the present invention is a business method of increasing value output of a fermentation plant, by performing a fermentation reaction using carbon-containing material in the presence of a modified microorganism to yield fermentation residual that has a higher commercial value than if the fermentation reaction were performed in the absence of the modified microorganisms. The nutrition enriched fermentation residuals lead to high nutritional content containing complete animal feeds. A preferable fermentation residuals produced according to the present invention has a higher commercial value than the conventional fermentation residuals. For example, the fermentation residuals can include enhanced dried solids such as DDGS with improved amino acid and other nutrient content.

The composition of the nutrient enriched fermentation residuals of the present invention differs from that of DDG and other distillers' co-products produced from the traditional dry mill ethanol production process, which are obtained through the fermentation of the starch present in whole, ground corn without the subject modified microorganisms. The nutrient enriched fermentation residual of this invention may have a nutrient content of from at least about 1% to about 95% by weight. The nutrient content is preferably in the range of at least about 10%-20%, 20%-30%, 30%-40%, 40%-50%, 50%-60%, and 60%-70% by weight.

In some embodiments of the business method, the feed composition comprises at least about 15% of fermentation residual by weight. In suitable embodiments, the feed composition comprises at least about 20%, at least about 25%, at least about 30%, at least about 35%, at least about 40%, at least about 45%, at least about 50%, at least about 60%, at least about 70%, or at least about 75%. Commonly, the feed composition comprises at least about 20% of fermentation residual by weight. More commonly, the feed composition comprises at least about 15-25%, 25-20%, 20-25%, 30%-40%, 40%-50%, 50%-60%, or 60%-70% by weight of fermentation residual. The feed compositions may additionally contain other nutrients, flavors, aromas, preservatives etc. The animal feed can also be tailor-made for a specific animal with specific nutrient needs.

The sale of distillers grain is an important part of the total profitability and is crucial to the growth of the ethanol industry. The effective marketing of distillers grain as animal feed would be essential to maintain the efficiency and profitability of the ethanol facilities. The animal feed can be used for any organism belonging to the kingdom Animalia and includes, without limitation, poultry, cattle, swine, goat, sheep, cat, dog, mouse, aquaculture, horse, and etc. The nutrient content of the animal feed can be modified by modifying the microorganisms in such a way that the microorganisms produce certain nutrients particular to an animal for which the feed is made. Therefore the animal feeds can be made for specific animal with specific nutrients, providing a whole breadth of the business market of animal feeds and thereby increasing the commercial value of the feed. Thus, the business method disclosed herein of marketing or selling one or more of the products of the fermentation reaction comprising the modified microorganism, would increase the value output of a fermentation plant.

In some embodiments of the business method, the increase in value output is achieved without substantially decreasing the amount of fermentation products that are produced by the fermentation reaction. The increase in production of the nutritional component by the modified microorganisms can be induced at a time when the fermentation has substantially been completed, preferably at least about 50% completed, more preferably at least about 70% completed, more preferably about 90% completed. Such regulation allows production of fermentation residuals of enhanced nutritional value without sacrificing the quantity of fermentation products such as alcohols and gaseous co-products. The completion of the fermentation reaction can be monitored by measuring the glucose content in the fermentation medium or measuring the gaseous products such as carbon dioxide.

In one embodiment of the business method, the fermentation residual has a shelf-life that is longer than that of a fermentation residual that is deficient in said modified microorganism. The fermentation residuals as such can be transported from a point of manufacture to a point of storage and further to a point of sale. At any point, it can be sold as is or is mixed to make a complete animal feed, which complete feed may comprise fermentation residuals, other nutrients, preservatives, flavors, and/or aromas etc. The shelf-life of the fermentation residuals can be increased by using nutrient enriched modified microorganisms which can be modified in such a way that the shelf-life of the fermentation residuals is longer. For example, microorganisms may be modified in such a way that the modified microorganism makes a compound that serves as a preservative. The shelf-life of the fermentation residuals can also be increased by employing a fermentation process that yields fermentation residuals that remain unspoiled in different weather, humidity, or temperature conditions. This process can include producing fermentation residuals as dry solid that has less moisture content and hence, is stable in warm weather conditions. The shelf-life of the fermentation residuals can be further increased by packing, storing and transporting the fermentation residuals in such a way that the fermentation residuals remain unspoiled.

In some embodiments of the business method, the microorganisms are modified in such a way that it is enriched in nutrients such as amino acids, preferably essential and/or limiting amino acids. Limiting amino acids may be supplied to an animal to increase production of a chosen animal product (e.g., milk) by supplementing the animal's feed with the limiting amino acid. Limiting amino acids may be identified by analyzing the amino acid profile of the chosen animal product (i.e., output profile) and comparing this profile to the profile of amino acids supplied to the animal (i.e., input profile). For example, cats require a high amount of taurine for their body functions, yet have limited enzymes which can produce taurine from other amino acids such as methionine and cysteine. Therefore, they need a diet high in taurine. If taurine is deficient, signs such as a heart condition called dilated cardiomyopathy, retinal degeneration, reproductive failure, and abnormal kitten development can occur. The complete feed of the invention containing modified microorganisms with high nutritional content can help treat or alleviate these disorders in animals. Therefore, complete animal feeds of the present invention can not only be made for different animals but it can also be made for animals deficient in a certain nutrient or animals which are suffering from one or more disorders related to the levels of nutrients in the body.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

EXAMPLES

Construction of Expression Vectors

An expression vector suitable for producing an exogenous sequence in a microorganism such as yeast cell is constructed according to standard recombinant techniques. The vector comprises a replication operon capable of replication in the yeast cell, an exogenous sequence of interest that is operably linked to a regulatory sequence controlling the expression. The vector is made optionally replicable in prokaryotes (i.e., a shuttle vector) such as bacteria to facilitate cloning. In addition, the vector comprises a regulatory sequence such as a glucose suppressor operon that normally suppresses the expression of the exogenous sequences and until when the glucose content in the medium is low or about to be depleted.

The expression vector is typically constructed to contain a selectable marker (for example, a gene encoding a protein necessary for the survival or growth of a host cell transformed with the vector), although such a marker gene can be carried on another polynucleotide sequence co-introduced into the host cell. Only those host cells into which a selectable gene has been introduced will survive and/or grow under selective conditions. Typical selection genes encode protein(s) that (a) confer resistance to antibiotics or other toxins substances, e.g., ampicillin, neomycin, methotrexate, etc.; (b) complement auxotrophic deficiencies; or (c) supply critical nutrients not available from complex media. The choice of the proper marker gene will depend on the host cell, and appropriate genes for different hosts are known in the art. Cloning and expression vectors also typically contain a replication system recognized by the host.

The exemplary expression vector is operatively linked to suitable transcriptional controlling elements, such as promoters, enhancers and terminators. For expression (i.e., translation), one or more translational controlling elements are also usually required, such as ribosome binding sites, translation initiation sites, and stop codons. These controlling elements (transcriptional and translational) may be derived from regulatory genes such as heat shock genes, genes implicated in toxicity and spore formation genes. A polynucleotide sequence encoding a signal peptide can also be included to allow the encoded exogenous sequence to cross and/or lodge in cell membranes or be secreted from the cell, if desired.

Expression of Exogenous Sequence (e.g. Enriched in One or More Essential Amino Acids):

The vectors containing the exogenous sequence of interest can be introduced into the yeast host cell by any of a number of appropriate means, including electroporation, transfection, bombardment, and infection. The transformed yeast cells are cultured in selective medium (e.g. with suitable antibiotics) to select those being transformed with the expression vector. A substantially homogenous culture of the transformants is then prepared for use in a fermentation reaction. Fermentation reaction is allowed to proceed under standard anaerobic conditions to yield alcohol and gaseous products. The residuals from the fermentation reaction contain the yeast transformants that have enhanced nutritional content, due to, e.g., overproduction of exogenous sequences that are enriched in one or more essential amino acids (e.g., lysine-rich).

What is claimed is:

1. A method of fermentation using carbon-containing material, comprising
    (a) mixing a carbon-containing material with a culture comprising genetically modified yeast cells that, in a fermentation reaction, produce an alcohol and a fermentation residual comprising a nutrient selected from the group consisting of an amino acid, a cofactor, a hormone, a protein, a vitamin and a lipid, wherein the yeast cells comprise a recombinant expression vector comprising an exogenous nucleotide sequence encoding a polypeptide and a regulatory sequence that controls the expression of the polypeptide, wherein the expression of said exogenous nucleotide sequence results in increased production of said polypeptide and said nutrient and enhanced concentration of the nutrient _ in the fermentation residual compared with the concentration of the nutrient in a fermentation residual produced by an unmodified corresponding yeast cell when used in the fermentation reaction;
    (b) fermenting the culture under conditions suitable for production of the alcohol and under conditions suitable for production the polypeptide and the nutrient;
    (c) separating the alcohol from the culture; and
    (d) producing the fermentation residual comprising the nutrient.

2. The method of claim 1, wherein the nutrient is an essential amino acid to at least one domesticated animal and the exogenous polypeptide comprises the essential amino acid.

3. The method of claim 2, wherein the essential amino acid is selected from the group consisting of lysine, methionine, phenylalanine, threonine, isoleucine, tryptophan, valine, leucine, arginine, taurine and histidine.

4. The method of claim 1, wherein the expression of the exogenous sequence is under the control of a regulatory sequence selected from the group consisting of a regulatory sequence of a heat shock gene, a regulatory sequence of a toxicity gene and a regulatory sequence of a spore formation gene.

5. The method of claim 1, wherein the exogenous nucleotide sequence modifies at least one of the structural genes in the nutrient's synthetic pathway.

6. The method of claim 1, wherein the exogenous nucleotide sequence modifies a regulatory control of the nutrient's synthetic pathway.

7. The method of claim 6, wherein the synthetic pathway is for an essential amino acid for a domesticated animal.

8. The method of claim 1, wherein the exogenous nucleotide sequence modifies a structural gene that regulates synthesis of a peptide containing at least one essential amino acid for a domesticated animal.

9. The method of claim 1, wherein the exogenous nucleotide sequence modifies the nutrient's transport processes out of or into the yeast cell.

10. The method of claim 1, wherein expression of the exogenous sequence is induced when the fermentation reaction has achieved at least about 50% completion.

11. The method of claim 1, wherein the nutrient is an essential amino acid to at least one domesticated animal.

12. The method of claim 11, wherein the essential amino acid is selected from the group consisting of lysine, methionine, phenylalanine, threonine, isoleucine, tryptophan, valine, leucine, arginine, taurine and histidine.

13. The method of claim 1, wherein the nutrient is a vitamin.

14. The method of claim 13, wherein the vitamin is selected from the group consisting of vitamin A, vitamin B1, vitamin B2, vitamin B3, vitamin B5, vitamin B6, vitamin B7, vitamin B9, vitamin B12, vitamin C, vitamin D1-D4, a tocopherol, and vitamin K.

15. The method of claim 1, wherein the nutrient is a lipid.

16. The method of claim 1, wherein the alcohol is ethanol.

17. The method of claim 1, wherein the alcohol is selected from the group consisting of methanol, propanol and butanol.

18. The method of claim 1, wherein the yeast is a *Saccharomyces*.

19. The method of claim 1, wherein the carbon-containing material is selected from the group consisting of cellulose, wood chips, vegetables, biomass, excreta, animal wastes, oat, wheat, corn, barley, milo, millet, rice, rye, sorghum, potato, sugar beets, taro, cassaya, fruits, fruit juices, and sugar cane.

20. The method of claim 1, wherein the fermentation residual comprises distillers dried grains.

21. The method of claim 1, wherein the fermentation residual comprises distillers dried grains with solubles.

22. The method of claim 1, further comprising incorporating the fermentation residual into animal feed.

23. The method of claim 16, further comprising mixing the ethanol with gasoline.

24. The method of claim 1, wherein the nutrient is produced when fermentation is at least about 95% completed.

* * * * *